(12) United States Patent  
Ikishima et al.

(10) Patent No.: US 8,552,182 B2
(45) Date of Patent: Oct. 8, 2013

(54) METHOD FOR PRODUCING A 3-(SUBSTITUTED-OXY)-4-PYRIDAZINOL DERIVATIVE

(75) Inventors: Hideaki Ikishima, Chiba (JP); Nobuhiro Kondo, Chiba (JP); Takeshi Takada, Omuta (JP); Yoshihisa Tsukamoto, Yasu (JP); Hidetake Yoshitomi, Omuta (JP); Haruko Mita, Omuta (JP)

(73) Assignee: Mitsui Chemicals Agro, Inc., Minato-Ku, Tokyo (JP)

( * ) Notice: Subject to any disclaimer, the term of this patent is extended or adjusted under 35 U.S.C. 154(b) by 20 days.

(21) Appl. No.: 13/498,550

(22) PCT Filed: Sep. 29, 2010

(86) PCT No.: PCT/JP2010/066917
§ 371 (c)(1),
(2), (4) Date: Mar. 27, 2012

(87) PCT Pub. No.: WO2011/040445
PCT Pub. Date: Apr. 7, 2011

(65) Prior Publication Data
US 2012/0184736 A1 Jul. 19, 2012

(30) Foreign Application Priority Data
Sep. 30, 2009 (JP) .................... 2009-226527

(51) Int. Cl.
*C07D 413/12* (2006.01)
*C07D 237/12* (2006.01)
(52) U.S. Cl.
USPC ......................... 544/114; 544/224
(58) Field of Classification Search
USPC ................. 544/114, 240, 224
See application file for complete search history.

(56) References Cited

U.S. PATENT DOCUMENTS

| 2005/0037925 A1 | 2/2005 | Tsukamoto et al. |
| 2008/0167461 A1 | 7/2008 | Tsukamoto et al. |

FOREIGN PATENT DOCUMENTS

| JP | 2004-002263 A | 1/2004 |
| JP | 2004-262936 A | 9/2004 |
| JP | 2008-239532 A | 10/2008 |
| WO | WO 2006/101058 | 9/2006 |

OTHER PUBLICATIONS

International Preliminary Report on Patentability (Form PCT/IB/373) and the Written Opinion of the International Searching Authority (Form PCT/ISA/237) issued on May 8, 2012, in the corresponding International Application No. PCT/JP2010/066917. (11 pages).

(Continued)

*Primary Examiner* — James O Wilson
*Assistant Examiner* — Cecilia M Jaisle
(74) *Attorney, Agent, or Firm* — Buchanan Ingersoll & Rooney PC

(57) ABSTRACT

A method for producing a 3-(substituted oxy)-4-pyridazinol compound represented by the following general formula (I):

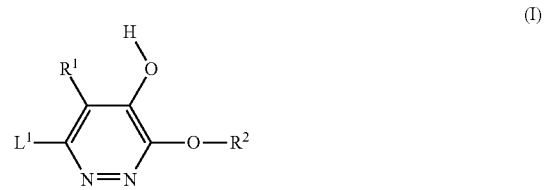

comprising reacting a compound represented by the following general formula (III):

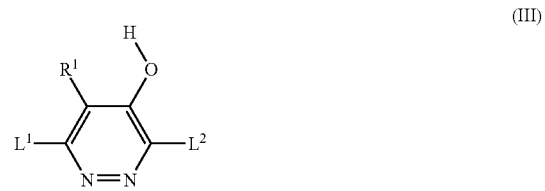

with a compound represented by the following general formula (IV):

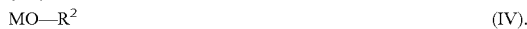

The compound represented by the general formula (I) can be reacted with a compound represented by the following general formula (VI):

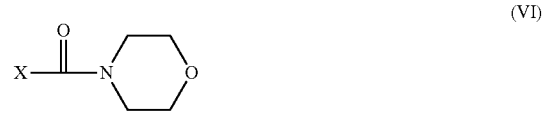

to provide a compound of general formula (V):

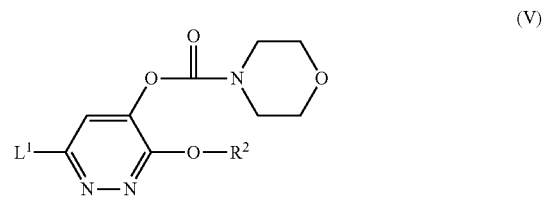

Each of the groups in the formulas is defined. The compounds of general formulas (I) and (V) can be obtained in a high yield and with high selectivity at a low cost, and therefore various functional and active substances can be advantageously synthesized using the compounds as a medicine, an agricultural chemical, a functional material, or an intermediate thereof.

17 Claims, No Drawings

(56) References Cited

OTHER PUBLICATIONS

International Search Report (PCT/ISA/210) issued on Nov. 2, 2010, by Japanese Patent Office as the International Searching Authority for International Application No. PCT/JP2010/066917.

G. Yadav et al., "Novelties of Solid—Liquid Phase Transfer Catalyzed Synthesis of Triclosan from Potassium 2,4-Dichlorophenolate and 2,5-Dichlorophenol", Industrial & Engineering Chemistry Research, 2008, vol. 47, No. 23, pp. 9055-9060.

The Chemical Society of Japan, The Fifth Series of Experimental Chemistry 14, 2nd print, Maruzen Co., Ltd., Apr. 15, 2007, pp. 241-249.

METHOD FOR PRODUCING A 3-(SUBSTITUTED-OXY)-4-PYRIDAZINOL DERIVATIVE

FIELD OF THE INVENTION

The present invention relates to a method for producing a 3-(substituted oxy)-4-pyridazinol derivative which is useful as medicines, agricultural chemicals, functional materials, or intermediates thereof. Further, the present invention is also related to a method for producing a 3-(substituted oxy)-4-pyridazinyl 4-morpholinecarboxylate using the 3-(substituted oxy)-4-pyridazinol derivative.

BACKGROUND ART

The 3-(substituted oxy)-4-pyridazinol derivative in the present invention is useful as medicines, agricultural chemicals, functional materials, or intermediates thereof. For example, 3-phenoxy-4-pyridazinol derivatives are known to have a herbicidal activity (patent document 1). Further, ester derivatives of 3-phenoxy-4-pyridazinol compounds are known to have a similar herbicidal activity (patent document 1). As an example of the compounds, 3-phenoxy-4-pyridazinyl 4-morpholinecarboxylate is described (patent document 1).

As methods for producing the pyridazinol derivative in the present invention, patent document 1 shows the following methods.

1) A method for producing a 6-chloro-3-phenoxy-4-pyridazinol derivative, which comprises reacting 3,6-dichloropyridazine with phenols to obtain a 3-chloro-6-phenoxy derivative, and then subjecting the pyridazine ring in the derivative to chlorination to obtain a 3,5-dichloro-6-phenoxypyridazine derivative, and hydrolyzing the obtained derivative to produce a 6-chloro-3-phenoxy-4-pyridazinol derivative. However, this method has reactions of three steps and has low selectivity in the chlorination, and cannot be a satisfying production method.

2) A method for producing a 3-phenoxy-4-pyridazinol derivative, which comprises oxidizing 3,6-dichloropyridazine using an oxidizing agent to provide 3,6-dichloropyridazine-1-oxide, and reacting the resultant oxide with a phenol derivative to obtain 6-chloro-3-phenoxypyridazine-1-oxide, and then subjecting the obtained compound to chlorination using phosphorus oxychloride to obtain a 3,5-dichloro-6-phenoxypyridazine derivative, and hydrolyzing the obtained derivative to produce a 3-phenoxy-4-pyridazinol derivative. However, this method has reactions of four steps and cannot be a satisfying production method.

3) A method for producing a 3-phenoxy-4-pyridazinol derivative, which comprises reacting 3,6-dichloropyridazine with phenols to obtain a 3-chloro-6-phenoxypyridazine derivative, and then oxidizing the obtained derivative using an oxidizing agent to obtain 6-chloro-3-phenoxypyridazin-1-oxide, and subsequently, subjecting the obtained compound to chlorination using phosphorus oxychloride to obtain a 3,5-dichloro-6-phenoxypyridazine derivative, and hydrolyzing the obtained derivative to produce a 3-phenoxy-4-pyridazinol derivative. However, this method has reactions of four steps and cannot be a satisfying production method.

4) A method for producing a 3-phenoxy-4-pyridazinol derivative, which comprises reacting 3,6-dichloro-4-methoxypyridazine with phenols to obtain a 3-phenoxy-4-methoxypyridazine derivative, and hydrolyzing the obtained derivative to produce a 3-phenoxy-4-pyridazinol derivative. In this method, however, a 3-phenoxy-5-methoxypyridazine derivative is produced as a main product in the first step, so that the yield of the 3-phenoxy-4-methoxypyridazine derivative which is a desired product is reduced, and thus this method cannot be a satisfying production method.

5) A method for producing a 6-chloro-3-phenoxy-4-pyridazinol derivative, which comprises reacting 3,6-dichloropyridazine with phenols to obtain a 3-chloro-6-phenoxypyridazine derivative, and then replacing the chlorine atom in the obtained derivative by a hydrogen atom using a reducing agent to obtain a 3-phenoxypyridazine derivative, and then oxidizing the obtained derivative using an oxidizing agent to obtain 3-phenoxypyridazin-1-oxide, and reacting the obtained compound with a metalation agent to effect metalation of the pyridazine ring at 6-position, and then reacting the resultant compound with an electrophile to introduce a chloro substituent or the like to the 6-position of the pyridazine ring, and subsequently, subjecting the resultant compound to chlorination using phosphorus oxychloride to obtain a 4,6-dichloro-3-phenoxypyridazine derivative, and hydrolyzing the obtained derivative to produce a 6-chloro-3-phenoxy-4-pyridazinol derivative. However, this method has reactions of seven steps and cannot be a satisfying production method.

6) A method for producing a 3-(2-hydroxyphenoxy)-4-pyridazinol derivative, which comprises reacting 3,4,6-trichloropyridazine with catechols, and then hydrolyzing the resultant 3-chloro[1,4]benzodioxino[2,3-c]pyridazine derivative to produce a 3-(2-hydroxyphenoxy)-4-pyridazinol derivative. However, this method has reactions of two steps, and further the derivative obtained by the method is limited to a 2-hydroxyphenoxy derivative, and this method cannot be a satisfying production method.

Further, patent document 1 has a description about a method for producing a 3-phenoxy-4-hydroxypyridazine derivative, which comprises reacting 4-hydroxypyridazine with phenols. However, this method is merely formally described and no specific example of the method is shown.

Patent document 1: Japanese Unexamined Patent Publication No. 2004-2263

DISCLOSURE OF THE INVENTION

Problems to be Solved by the Invention

In view of the importance of the 3-(substituted oxy)-4-pyridazinol derivative which is useful as medicines, agricultural chemicals, functional materials, or intermediates thereof, the present inventors have made extensive and intensive studies with a view toward developing a method for synthesizing the derivative with ease.

As a result, the present inventors have found that, by reacting a 4-pyridazinol derivative (III) with a hydroxy derivative (IV) in the presence or absence of a base and in the presence or absence of a solvent, a 3-(substituted oxy)-4-pyridazinol derivative (I) can be selectively obtained, and the present invention has been completed.

The present invention has the following characteristic features.

1) The hydroxy derivative (IV) is negatively charged in the presence of a base due to the proton abstraction. The 4-pyridazinol derivative (III) is also negatively charged in the presence of a base due to the proton abstraction. The two compounds negatively charged, which are generally unlikely to undergo a reaction, are reacted with each other in the present invention.

2) Almost no reaction is caused between the 4-pyridazinol derivatives (III) or between the hydroxy derivatives (IV), and a reaction between the 4-pyridazinol derivative (III) and the hydroxy derivative (IV) is selectively caused.

3) Though the 4-pyridazinol derivative (III) has reaction sites at 3- and 6-positions, the hydroxy derivative (IV) is selectively reacted with the 3-position of the 4-pyridazinol derivative (III).

Means to Solve the Problems

The present invention is directed to a method for producing a 3-(substituted oxy)-4-pyridazinol derivative represented by the following general formula (I):

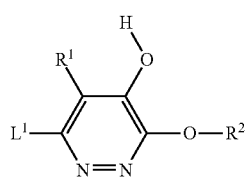

(I)

wherein:
$R^1$ represents a hydrogen atom, a halogen atom, a $C_1$-$C_3$ alkyl group, a ($C_1$-$C_3$ alkoxy)$C_1$-$C_3$ alkyl group, or a tri($C_1$-$C_3$ alkyl)silyl group;
$R^2$ represents a $C_1$-$C_6$ alkyl group, a $C_1$-$C_6$ haloalkyl group, a $C_3$-$C_6$ cycloalkyl group, a $C_2$-$C_6$ alkenyl group, a ($C_1$-$C_6$ alkoxy)$C_1$-$C_6$ alkyl group, a 5- or 6-membered heterocyclic group (in which the heterocycle contains in the ring thereof one of a nitrogen atom, an oxygen atom, or a sulfur atom and optionally further contains 1 to 2 nitrogen atoms), or an optionally substituted phenyl group represented by the following general formula (II):

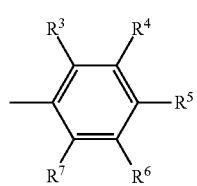

(II)

wherein, in the general formula (II), each of $R^3$, $R^4$, $R^5$, $R^6$, and $R^7$ independently represents a hydrogen atom, a fluorine atom, a chlorine atom, a bromine atom, an iodine atom, an optionally substituted $C_1$-$C_4$ alkyl group (in which the substituent is 1 to 3 substituents which are selected from the group consisting of a fluorine atom, a chlorine atom, and a bromine atom, and which are the same or different, or a $C_3$-$C_4$ cycloalkyl group, a $C_1$-$C_3$ alkylthio group, or a $C_1$-$C_3$ alkoxyimino group), a $C_2$-$C_3$ alkenyl group, a $C_2$-$C_3$ alkynyl group, an optionally substituted $C_3$-$C_5$ cycloalkyl group (in which the substituent is 1 to 3 substituents which are selected from the group consisting of a fluorine atom, a chlorine atom, a bromine atom, a $C_1$-$C_3$ alkyl group, a $C_3$-$C_4$ cycloalkyl group, a cyano group, a $C_1$-$C_3$ alkoxy group, and a $C_1$-$C_3$ alkylthio group, and which are the same or different), a $C_6$-$C_7$ bicycloalkyl group, a cyano group, a $C_2$-$C_4$ alkylcarbonyl group, a $C_2$-$C_4$ alkoxycarbonyl group, an optionally substituted phenyl group {in which the substituent is a fluorine atom, a chlorine atom, a bromine atom, a $C_1$-$C_3$ alkyl group, or a $C_1$-$C_3$ haloalkyl group (in which the halogen atom is 1 to 3 halogen atoms which are selected from the group consisting of a fluorine atom, a chlorine atom, and a bromine atom, and which are the same or different)}, an optionally substituted 5- or 6-membered heterocyclic group {in which the heterocycle contains in the ring thereof one of a nitrogen atom, an oxygen atom, or a sulfur atom and optionally further contains 1 to 2 nitrogen atoms, and the substituent is 1 to 2 substituents which are selected from the group consisting of a fluorine atom, a chlorine atom, a bromine atom, a $C_1$-$C_3$ alkyl group, and a $C_1$-$C_3$ haloalkyl group (in which the halogen atom is 1 to 3 halogen atoms which are selected from the group consisting of a fluorine atom, a chlorine atom, and a bromine atom, and which are the same or different), and which are the same or different}, a nitro group, a $C_1$-$C_3$ alkoxy group, a $C_1$-$C_3$ haloalkoxy group (in which the halogen atom is 1 to 3 halogen atoms which are selected from the group consisting of a fluorine atom, a chlorine atom, and a bromine atom, and which are the same or different), an optionally substituted phenoxy group (in which the substituent is a pyridazinyloxy group substituted with 1 to 3 substituents which are selected from the group consisting of a fluorine atom, a chlorine atom, a bromine atom, and a $C_1$-$C_3$ alkoxy group, and which are the same or different), or a $C_1$-$C_3$ alkylthio group, or the group which the adjacent two of $R^3$, $R^4$, $R^5$, $R^6$, and $R^7$ taken together form is a group represented by the formula:
—$CH_2CH_2$—, —$CH_2CH_2CH_2$—, —$CH(CH_3)$$CH_2CH_2$—, —$CH_2CH_2CH_2CH_2$—, —CH=CH—CH=CH—, —$OCH_2CH_2$—, —OCH=CH—, —OCH=C($CH_3$)—, —SCH=CH—, —N=CH—CH=CH—, —$OCH_2$O—, —$OCH_2CH_2$O—,

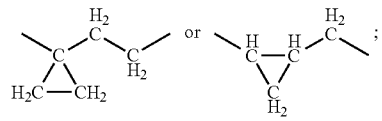

and
$L^1$ represents a halogen atom, a cyano group, an $OR^8$ group {wherein $R^8$ is an optionally substituted phenyl group (in which the substituent is 1 to 3 substituents which are selected from the group consisting of a nitro group, a trifluoromethyl group, and a cyano group, and which are the same or different)}, an $SO_2R^9$ group {wherein $R^9$ is a $C_1$-$C_6$ alkyl group, a $C_1$-$C_6$ haloalkyl group, or an optionally substituted phenyl group (in which the substituent is 1 to 3 substituents which are selected from the group consisting of a $C_1$-$C_6$ alkyl group, a halogen atom, a nitro group, a trifluoromethyl group, and a cyano group, and which are the same or different)}, a nitro group, an imidazolyl group, or a pyrazolyl group,
the method comprising:
reacting a compound represented by the following general formula (III):

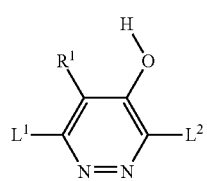

(III)

wherein $R^1$ and $L^1$ are as defined above, and $L^2$ has the same
meaning as that of $L^1$, and $L^1$ and $L^2$ are the same or different with a compound represented by the following general formula (IV):

MO—$R^2$ (IV)

wherein M represents a hydrogen atom or an alkali metal, and $R^2$ is defined above
in the presence or absence of a base and in the presence or absence of a solvent to produce a 3-(substituted oxy)-4-pyridazinol derivative represented by the general formula (I).

Further, in the present invention, provided is also a method for producing, using the 3-(substituted oxy)-4-pyridazinol derivative (I), a 3-(substituted oxy)-4-pyridazinyl 4-morpholinecarboxylate represented by the following general formula (V):

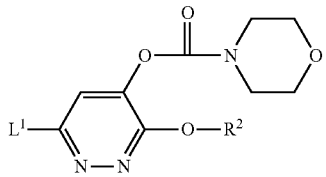

wherein $R^2$ and $L^1$ are as defined above.

Effect of the Invention

By the method of the present invention, a 3-(substituted oxy)-4-pyridazinol derivative (I) and a 3-(substituted oxy)-4-pyridazinyl 4-morpholinecarboxylate (V), which are useful as medicines, agricultural chemicals, functional materials, or intermediates thereof, can be stably produced with high selectivity at a low cost.

BEST MODE FOR CARRYING OUT THE INVENTION

Hereinbelow, the compounds used in the method of the present invention and the compound in the present invention will be described.

In the present invention, the "halogen atom" is a fluorine atom, a chlorine atom, a bromine atom, or an iodine atom, preferably a fluorine atom, a chlorine atom, or a bromine atom, more preferably a chlorine atom or a bromine atom, further more preferably a chlorine atom.

In the present invention, the "$C_1$-$C_3$ alkyl group" is a linear or branched alkyl group having 1 to 3 carbon atoms, and can be, for example, methyl, ethyl, propyl, or isopropyl, and is more preferably an alkyl group having 1 to 2 carbon atoms ($C_1$-$C_2$ alkyl group), especially preferably a methyl group.

In the present invention, the "$C_1$-$C_3$ alkoxy group" is a linear or branched alkoxy group having 1 to 3 carbon atoms, and can be, for example, methoxy, ethoxy, propoxy, or isopropoxy, and is preferably a methoxy or ethoxy group, more preferably a methoxy group.

In the present invention, the "($C_1$-$C_3$ alkoxy)$C_1$-$C_3$ alkyl group" is the "$C_1$-$C_3$ alkyl group" substituted with the one "$C_1$-$C_3$ alkoxy group", and can be, for example, a methoxymethyl, ethoxymethyl, propoxymethyl, methoxyethyl, ethoxyethyl, propoxyethyl, butoxyethyl, or methoxypropyl group, and is preferably a methoxyethyl, ethoxyethyl, or ethoxymethyl group.

In the present invention, the "tri($C_1$-$C_3$ alkyl)silyl group" is a silicon atom having bonded thereto the three "$C_1$-$C_3$ alkyl groups" which are the same or different, and can be, for example, a trimethylsilyl, triethylsilyl, triisopropylsilyl, or dimethylisopropylsilyl group, and is preferably a trimethylsilyl or dimethylisopropylsilyl group, more preferably a trimethylsilyl group.

In the present invention, the "$C_1$-$C_6$ alkyl group" is a linear or branched alkyl group having 1 to 6 carbon atoms, and can be, for example, a methyl, ethyl, propyl, isopropyl, butyl, isobutyl, s-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, or 2-ethylbutyl group, and is preferably a linear or branched alkyl group having 1 to 4 carbon atoms ($C_1$-$C_4$ alkyl group), more preferably a linear or branched alkyl group having 1 to 3 carbon atoms ($C_1$-$C_3$ alkyl group), further more preferably an alkyl group having 1 to 2 carbon atoms ($C_1$-$C_2$ alkyl group), especially preferably a methyl group.

In the present invention, the "$C_1$-$C_6$ haloalkyl group" is the "$C_1$-$C_6$ alkyl group" substituted with the 1 to 5 "halogen atoms" which are the same or different, and can be, for example, a chloromethyl, dichloromethyl, trichloromethyl, 1-chloroethyl, 2-chloroethyl, 2,2,2-trichloroethyl, 1-chloropropyl, 3-chloropropyl, 1-chlorobutyl, 4-chlorobutyl, fluoromethyl, difluoromethyl, trifluoromethyl, 1-fluoroethyl, 2-fluoroethyl, 2,2,2-trifluoroethyl, pentafluoroethyl, fluorochloromethyl, bromomethyl, 1-bromoethyl, 2-bromoethyl, or iodomethyl group, and is preferably a $C_1$-$C_3$ alkyl group substituted with 1 to 3 substituents which are selected from the group consisting of a fluorine atom, a chlorine atom, and a bromine atom, and which are the same or different, more preferably a $C_1$-$C_2$ alkyl group substituted with 1 to 3 fluorine atoms or chlorine atoms which are the same, further more preferably a fluoromethyl, difluoromethyl, trifluoromethyl, or 2,2,2-trichloroethyl group, especially preferably a trifluoromethyl group.

In the present invention, the "$C_3$-$C_6$ cycloalkyl group" is a cyclopropyl, cyclobutyl, cyclopentyl, or cyclohexyl group, preferably a cyclopropyl or cyclobutyl group, more preferably a cyclopropyl group.

In the present invention, the "$C_2$-$C_6$ alkenyl group" is a linear or branched alkenyl group having 2 to 6 carbon atoms, and can be, for example, a vinyl, 1-methylvinyl, allyl, 1-propenyl, 1-methyl-1-propenyl, 2-propenyl, 1-methyl-2-propenyl, 2-methyl-2-propenyl, 2-ethyl-2-propenyl, 2-butenyl, 1-methyl-2-butenyl, 2-methyl-2-butenyl, 1-ethyl-2-butenyl, 3-butenyl, 1-methyl-3-butenyl, 2-methyl-3-butenyl, 1-ethyl-3-butenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 2-hexenyl, 3-hexenyl, 4-hexenyl, or 5-hexenyl group, and is preferably a linear or branched alkenyl group having 2 to 4 carbon atoms ($C_2$-$C_4$ alkenyl group), more preferably a vinyl, 1-methylvinyl, allyl, 2-propenyl, or 1-methyl-2-propenyl group.

In the present invention, the "$C_1$-$C_6$ alkoxy group" is a linear or branched alkoxy group having 1 to 6 carbon atoms, and can be, for example, a methoxy, ethoxy, propoxy, isopropoxy, butoxy, isobutoxy, s-butoxy, t-butoxy, pentoxy, isopentoxy, 2-methylbutoxy, neopentoxy, 1-ethylpropoxy, hexyloxy, 4-methylpentoxy, 3-methylpentoxy, 2-methylpentoxy, 1-methylpentoxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy, or 2-ethylbutoxy group, and is preferably a linear or branched alkoxy group having 1 to 3 carbon atoms ($C_1$-$C_3$ alkoxy group), more preferably a methoxy or ethoxy group, further more preferably a methoxy group.

In the present invention, the "($C_1$-$C_6$ alkoxy)$C_1$-$C_6$ alkyl group" is the "$C_1$-$C_6$ alkyl group" substituted with the one "$C_1$-$C_6$ alkoxy group", and can be, for example, a methoxymethyl, ethoxymethyl, propoxymethyl, butoxymethyl, s-butoxymethyl, t-butoxymethyl, pentyloxymethyl, hexyloxymethyl, methoxyethyl, ethoxyethyl, propoxyethyl, butoxyethyl, methoxypropyl, methoxybutyl, methoxypentyl, or methoxyhexyl group, and is preferably a $C_1$-$C_6$ alkyl group substituted with one $C_1$-$C_3$ alkoxy group, more preferably a methoxyethyl, ethoxyethyl, or ethoxymethyl group.

In the present invention, the "5- or 6-membered heterocyclic group (in which the heterocycle contains in the ring thereof one of a nitrogen atom, an oxygen atom, or a sulfur atom and optionally further contains 1 to 2 nitrogen atoms)" is a 5- or 6-membered heterocyclic group containing one of a nitrogen atom, an oxygen atom, or a sulfur atom as a heteroatom and optionally further containing 1 to 2 nitrogen atoms, and can be, for example, a furyl, thienyl, pyrrolyl, pyrazolyl, imidazolyl, isoxazolyl, oxazolyl, isothiazolyl, thiazolyl, triazolyl, pyranyl, pyridyl, pyrazinyl, pyrimidinyl, pyridazinyl, or triazinyl group, and is preferably a 5-membered heterocyclic group (in which the heterocycle contains in the ring thereof one of a nitrogen atom, an oxygen atom, or a sulfur atom), more preferably a furyl or thienyl group.

In the present invention, the "$C_1$-$C_4$ alkyl group" is a linear or branched alkyl group having 1 to 4 carbon atoms, and can be, for example, a methyl, ethyl, propyl, isopropyl, butyl, isobutyl, s-butyl, or t-butyl group, and is preferably a linear or branched alkyl group having 1 to 3 carbon atoms ($C_1$-$C_3$ alkyl group), further more preferably an alkyl group having 1 to 2 carbon atoms ($C_1$-$C_2$ alkyl group), especially preferably a methyl group.

In the present invention, the "$C_3$-$C_4$ cycloalkyl group" is a cyclopropyl or cyclobutyl group, preferably a cyclopropyl group.

In the present invention, the "$C_1$-$C_3$ alkylthio group" is a linear or branched alkylthio group having 1 to 3 carbon atoms, and can be, for example, a methylthio, ethylthio, propylthio, or isopropylthio group, and is preferably a methylthio or ethylthio group, further more preferably a methylthio group.

In the present invention, the "$C_1$-$C_3$ alkoxyimino group" is a linear or branched alkoxyimino group having 1 to 3 carbon atoms, and can be, for example, a methoxyimino, ethoxyimino, propoxyimino, or isopropoxyimino group, and is preferably a methoxyimino or ethoxyimino group, further more preferably a methoxyimino group.

In the present invention, the "optionally substituted $C_1$-$C_4$ alkyl group (in which the substituent is 1 to 3 substituents which are selected from the group consisting of a fluorine atom, a chlorine atom, and a bromine atom, and which are the same or different, a $C_3$-$C_4$ cycloalkyl group, a $C_1$-$C_3$ alkylthio group, or a $C_1$-$C_3$ alkoxyimino group)" is the "$C_1$-$C_4$ alkyl group" optionally substituted with 1 to 3 substituents which are selected from the group consisting of a fluorine atom, a chlorine atom, and a bromine atom, and which are the same or different, or the at least one "$C_3$-$C_4$ cycloalkyl group", "$C_1$-$C_3$ alkylthio group", or "$C_1$-$C_3$ alkoxyimino group", and can be, for example, a fluoromethyl, difluoromethyl, trifluoromethyl, 2,2,2-trichloroethyl, cyclopropylmethyl, methylthiomethyl, methylthioethyl, ethylthiomethyl, ethylthioethyl, or methoxyiminomethyl group, and is preferably a $C_1$-$C_2$ alkyl group substituted with 1 to 3 fluorine atoms or chlorine atoms which are the same, or a $C_1$-$C_2$ alkyl group optionally substituted with a cyclopropyl group, a $C_1$-$C_2$ alkylthio group, or a $C_1$-$C_2$ alkoxyimino group.

In the present invention, the "$C_2$-$C_3$ alkenyl group" is a linear or branched alkenyl group having 2 to 3 carbon atoms, and can be, for example, vinyl, 1-methylvinyl, allyl, or 1-propenyl, and is preferably a vinyl, 1-methylvinyl, or allyl group.

In the present invention, the "$C_2$-$C_3$ alkynyl group" is an alkynyl group having 2 to 3 carbon atoms, and can be, for example, ethynyl, 2-propynyl, or 1-methyl-2-propynyl, and is preferably an ethynyl group.

In the present invention, the "$C_3$-$C_5$ cycloalkyl group" is a cyclopropyl, cyclobutyl, or cyclopentyl group, and is preferably a cyclopropyl or cyclobutyl group, more preferably a cyclopropyl group.

In the present invention, the "optionally substituted $C_3$-$C_5$ cycloalkyl group (in which the substituent is 1 to 3 substituents which are selected from the group consisting of a fluorine atom, a chlorine atom, a bromine atom, a $C_1$-$C_3$ alkyl group, a $C_3$-$C_4$ cycloalkyl group, a cyano group, a $C_1$-$C_3$ alkoxy group, and a $C_1$-$C_3$ alkylthio group, and which are the same or different)" is the "$C_3$-$C_5$ cycloalkyl group" substituted with 1 to 3 substituents which are selected from the group consisting of a fluorine atom, a chlorine atom, a bromine atom, the "$C_1$-$C_3$ alkyl group", the "$C_3$-$C_4$ cycloalkyl group", a cyano group, the "$C_1$-$C_3$ alkoxy group", and the "$C_1$-$C_3$ alkylthio group", and which are the same or different, and can be, for example, a fluorocyclopropyl, difluorocyclopropyl, chlorocyclopropyl, dichlorocyclopropyl, bromocyclopropyl, dibromocyclopropyl, methylcyclopropyl, ethylcyclopropyl, propylcyclopropyl, isopropylcyclopropyl, cyanocyclopropyl, cyclopropylcyclopropyl, cyclobutylcyclopropyl, methoxycyclopropyl, ethoxycyclopropyl, methylthiocyclopropyl, ethylthiocyclopropyl, dimethylcyclopropyl, methyl(ethyl)cyclopropyl, diethylcyclopropyl, biscyanocyclopropyl, trimethylcyclopropyl, tetramethylcyclopropyl, pentamethylcyclopropyl, methylcyclobutyl, or cyanocyclobutyl group, and is preferably a $C_3$-$C_4$ cycloalkyl group substituted with 1 to 3 substituents which are selected from the group consisting of a fluorine atom, a chlorine atom, a bromine atom, a $C_1$-$C_3$ alkyl group, a $C_3$-$C_4$ cycloalkyl group, a cyano group, a $C_1$-$C_3$ alkoxy group, and a $C_1$-$C_3$ alkylthio group, and which are the same or different, more preferably a cyclopropyl group substituted with 1 to 3 substituents which are selected from the group consisting of a chlorine atom, a bromine atom, a $C_1$-$C_2$ alkyl group, a cyclopropyl group, a cyano group, a $C_1$-$C_2$ alkoxy group, and a $C_1$-$C_2$ alkylthio group, and which are the same or different.

In the present invention, the "$C_6$-$C_7$ bicycloalkyl group" is a bicyclic hydrocarbon having 6 to 7 carbon atoms, and can be, for example, bicyclohexyl or bicycloheptyl, and is preferably a bicyclo[3.1.0]hexyl or bicyclo[4.1.0]heptyl group, more preferably a bicyclo[3.1.0]hexan-6-yl group.

In the present invention, the "$C_2$-$C_4$ alkylcarbonyl group" is a carbonyl group having bonded thereto the "$C_1$-$C_3$ alkyl group", and can be, for example, an acetyl, propionyl, butyryl, or isobutyryl group, and is preferably an acetyl or propionyl group, most preferably an acetyl group.

In the present invention, the "$C_2$-$C_4$ alkoxycarbonyl group" is a carbonyl group having bonded thereto the "$C_1$-$C_3$ alkoxy group", and can be, for example, a methoxycarbonyl, ethoxycarbonyl, propoxycarbonyl, or isopropoxycarbonyl group, and is preferably a methoxycarbonyl or ethoxycarbonyl group, more preferably a methoxycarbonyl group.

In the present invention, the "$C_1$-$C_3$ haloalkyl group (in which the halogen atom is 1 to 3 halogen atoms which are selected from the group consisting of a fluorine atom, a chlorine atom, and a bromine atom, and which are the same or different)" is the "$C_1$-$C_3$ alkyl group" substituted with 1 to 3 halogen atoms which are selected from the group consisting of a fluorine atom, a chlorine atom, and a bromine atom, and which are the same or different, and can be, for example, a chloromethyl, dichloromethyl, trichloromethyl, 1-chloroethyl, 2-chloroethyl, 2,2,2-trichloroethyl, 1-chloropropyl, 3-chloropropyl, 1-chlorobutyl, 4-chlorobutyl, fluoromethyl, difluoromethyl, trifluoromethyl, 1-fluoroethyl, 2-fluoroethyl, 2,2,2-trifluoroethyl, pentafluoroethyl, fluorochloromethyl, bromomethyl, 1-bromoethyl, or 2-bromoethyl group, and is preferably a $C_1$-$C_2$ alkyl group substituted with 1 to 3 fluorine atoms or chlorine atoms which are the same, more preferably a fluoromethyl, difluoromethyl, trifluoromethyl, or 2,2,2-trichloroethyl group, further preferably a trifluoromethyl group.

In the present invention, the "optionally substituted phenyl group {in which the substituent is a fluorine atom, a chlorine atom, a bromine atom, a $C_1$-$C_3$ alkyl group, or a $C_1$-$C_3$ haloalkyl group (in which the halogen atom is 1 to 3 halogen atoms which are selected from the group consisting of a fluorine atom, a chlorine atom, and a bromine atom, and which are the same or different)}" is a phenyl group optionally substituted with a fluorine atom, a chlorine atom, a bromine atom, the "$C_1$-$C_3$ alkyl group", or the "$C_1$-$C_3$ haloalkyl group (in which the halogen atom is 1 to 3 halogen atoms which are selected from the group consisting of a fluorine atom, a chlorine atom, and a bromine atom, and which are the same or different)", and can be, for example, a phenyl, fluorophenyl, chlorophenyl, methylphenyl, ethylphenyl, cyclopropylphenyl, or (trifluoromethyl)phenyl group, and is preferably a phenyl, chlorophenyl, methylphenyl, or (trifluoromethyl)phenyl group.

In the present invention, the "optionally substituted 5- or 6-membered heterocyclic group {in which the heterocycle contains in the ring thereof one of a nitrogen atom, an oxygen atom, or a sulfur atom and optionally further contains 1 to 2 nitrogen atoms, and the substituent is 1 to 2 substituents which are selected from the group consisting of a fluorine atom, a chlorine atom, a bromine atom, a $C_1$-$C_3$ alkyl group, and a $C_1$-$C_3$ haloalkyl group (in which the halogen atom is 1 to 3 halogen atoms which are selected from the group consisting of a fluorine atom, a chlorine atom, and a bromine atom, and which are the same or different), and which are the same or different}" is the "5- or 6-membered heterocyclic group (in which the heterocycle contains in the ring thereof one of a nitrogen atom, an oxygen atom, or a sulfur atom and optionally further contains 1 to 2 nitrogen atoms)" which is optionally substituted with a fluorine atom, a chlorine atom, a bromine atom, the "$C_1$-$C_3$ alkyl group", or the "$C_1$-$C_3$ haloalkyl group (in which the halogen atom is 1 to 3 halogen atoms which are selected from the group consisting of a fluorine atom, a chlorine atom, and a bromine atom, and which are the same or different)", and is preferably a pyrrolyl, furyl, thienyl, pyrazolyl, thiazolyl, or pyridyl group optionally substituted with 1 to 2 substituents which are selected from the group consisting of a chlorine atom, a bromine atom, a methyl group, an ethyl group, and a trifluoromethyl group, and which are the same, further more preferably a thienyl, pyrazolyl, or thiazolyl group optionally substituted with 1 to 2 substituents which are selected from the group consisting of a chlorine atom, a methyl group, and a trifluoromethyl group, and which are the same or different.

In the present invention, the "$C_1$-$C_3$ haloalkoxy group (in which the halogen atom is 1 to 3 halogen atoms which are selected from the group consisting of a fluorine atom, a chlorine atom, and a bromine atom, and which are the same or different)" is the "$C_1$-$C_3$ alkoxy group" substituted with 1 to 3 halogen atoms which are selected from the group consisting of a fluorine atom, a chlorine atom, and a bromine atom, and which are the same or different, and can be, for example, a chloromethoxy, dichloromethoxy, trichloromethoxy, 1-chloroethoxy, 2-chloroethoxy, 2,2,2-trichloroethoxy, 1-chloropropoxy, 3-chloropropoxy, fluoromethoxy, difluoromethoxy, trifluoromethoxy, 1-fluoroethoxy, 2-fluoroethoxy, 2,2,2-trifluoroethoxy, fluorochloromethoxy, bromomethoxy, 1-bromoethoxy, or 2-bromoethoxy group, and is preferably a $C_1$-$C_2$ alkoxy group substituted with 1 to 3 fluorine atoms or chlorine atoms which are the same, more preferably a fluoromethoxy, difluoromethoxy, trifluoromethoxy, or 2,2,2-trichloroethoxy group, further preferably a trifluoromethoxy group.

In the present invention, the "optionally substituted phenoxy group (in which the substituent is a pyridazinyloxy group substituted with 1 to 3 substituents which are selected from the group consisting of a fluorine atom, a chlorine atom, a bromine atom, and a $C_1$-$C_3$ alkoxy group, and which are the same or different)" is a phenoxy group which is substituted with a pyridazinyloxy group substituted with 1 to 3 substituents which are selected from the group consisting of a fluorine atom, a chlorine atom, a bromine atom, and the "$C_1$-$C_3$ alkoxy group", and which are the same or different, and is preferably a phenoxy group which is substituted with a pyridazinyloxy group substituted with each of a chlorine atom and a methoxy or ethoxy group.

In the present invention, the "group which the adjacent two of $R^3$, $R^4$, $R^5$, $R^6$, and $R^7$ taken together form" is preferably a group represented by the formula: —$CH_2CH_2CH_2$—, —$CH(CH_3)CH_2CH_2$—, —$OCH_2CH_2$—, —$OCH=CH$—, or

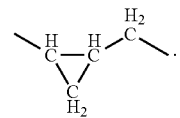

In the present invention, the "optionally substituted phenyl group (in which the substituent is 1 to 3 substituents which are selected from the group consisting of a nitro group, a trifluoromethyl group, and a cyano group, and which are the same or different)" is a phenyl group optionally substituted with 1 to 3 substituents which are selected from the group consisting of a nitro group, a trifluoromethyl group, and a cyano group, and which are the same or different, and can be, for example, phenyl, nitrophenyl, (trifluoromethyl)phenyl, cyanophenyl, dinitrophenyl, or trinitrophenyl, and is preferably a phenyl, nitrophenyl, (trifluoromethyl)phenyl, or dinitrophenyl group.

In the present invention, the "optionally substituted phenyl group (in which the substituent is 1 to 3 substituents which are selected from the group consisting of a $C_1$-$C_6$ alkyl group, a halogen atom, a nitro group, and a trifluoromethyl group, and which are the same or different)" is a phenyl group optionally substituted with 1 to 3 substituents which are selected from the group consisting of the "$C_1$-$C_6$ alkyl group", the "halogen atom", a nitro group, and a trifluoromethyl group, and which are the same or different, and can be, for example, phenyl, tolyl, ethylphenyl, fluorophenyl, chlorophenyl, bromophenyl, nitrophenyl, dinitrophenyl, trinitrophenyl, or (trifluoromethyl)phenyl, and is preferably a phenyl, tolyl, chlorophenyl, nitrophenyl, or (trifluoromethyl)phenyl group.

The compound (I) in the present invention can be in the form of a salt, and the salt can be, for example, an alkali metal salt, an alkaline earth metal salt, an ammonium salt, or an organic amine salt, and when the compound has a basic moiety in the molecule thereof, the salt can be, for example, a sulfate, a hydrochloride, a nitrate, or a phosphate.

With respect to the compound (I) in the present invention, the "alkali metal salt" can be, for example, a sodium salt, a potassium salt, or a lithium salt, and is preferably a sodium salt or a potassium salt.

With respect to the compound (I) in the present invention, the "alkaline earth metal salt" can be, for example, a calcium salt or a magnesium salt, and is preferably a magnesium salt.

With respect to the compound (I) in the present invention, the "organic amine salt" can be, for example, a methylamine salt, a diethylamine salt, a trimethylamine salt, a triethylamine salt, a diisopropylamine salt, a tributylamine salt, a 1,4-diazabicyclo[2.2.2]octane (DABCO) salt, a 1,8-diazabicyclo[5.4.0]undec-7-ene (DBU) salt, a pyridine salt, a collidine salt, a 4-(N,N-dimethylamino)pyridine salt, a pyrrolidine salt, a piperidine salt, a piperazine salt, a morpholine salt, or an N-methylmorpholine salt, and is preferably a triethylamine salt or a pyridine salt.

A solvate of the compound (I) in the present invention is also included in the present invention.

The compound (I) in the present invention may be a compound having an asymmetric carbon, and, in such a case, the compound (I) in the present invention includes an optically active compound and a mixture of two or more optically active compounds in an arbitrary proportion.

In the compound (I) and the like in the present invention, (1a) $R^1$ is preferably a hydrogen atom, (2a) $R^2$ is preferably an optionally substituted phenyl group represented by the general formula (II), wherein, in the general formula (II), each of $R^3$, $R^4$, $R^5$, $R^6$, and $R^7$ is independently a hydrogen atom, a fluorine atom, a chlorine atom, a bromine atom, an iodine atom, an optionally substituted $C_1$-$C_4$ alkyl group (in which the substituent is 1 to 3 substituents which are selected from the group consisting of a fluorine atom, a chlorine atom, and a bromine atom, and which are the same or different, or a $C_3$-$C_4$ cycloalkyl group, a $C_1$-$C_3$ alkylthio group, or a $C_1$-$C_3$ alkoxyimino group), a $C_2$-$C_3$ alkenyl group, a $C_2$-$C_3$ alkynyl group, an optionally substituted $C_3$-$C_5$ cycloalkyl group (in which the substituent is 1 to 3 substituents which are selected from the group consisting of a fluorine atom, a chlorine atom, a bromine atom, a $C_1$-$C_3$ alkyl group, a $C_3$-$C_4$ cycloalkyl group, a cyano group, a $C_1$-$C_3$ alkoxy group, and a $C_1$-$C_3$ alkylthio group, and which are the same or different), a $C_6$-$C_7$ bicycloalkyl group, a cyano group, a $C_2$-$C_4$ alkylcarbonyl group, a $C_2$-$C_4$ alkoxycarbonyl group, an optionally substituted phenyl group {in which the substituent is a fluorine atom, a chlorine atom, a bromine atom, a $C_1$-$C_3$ alkyl group, or a $C_1$-$C_3$ haloalkyl group (in which the halogen atom is 1 to 3 halogen atoms which are selected from the group consisting of a fluorine atom, a chlorine atom, and a bromine atom, and which are the same or different) an optionally substituted 5- or 6-membered heterocyclic group {in which the heterocycle contains in the ring thereof one of a nitrogen atom, an oxygen atom, or a sulfur atom and optionally further contains 1 to 2 nitrogen atoms, and the substituent is 1 to 2 substituents which are selected from the group consisting of a fluorine atom, a chlorine atom, a bromine atom, a $C_1$-$C_3$ alkyl group, and a $C_1$-$C_3$ haloalkyl group (in which the halogen atom is 1 to 3 halogen atoms which are selected from the group consisting of a fluorine atom, a chlorine atom, and a bromine atom, and which are the same or different)}, a nitro group, a $C_1$-$C_3$ alkoxy group, a $C_1$-$C_3$ haloalkoxy group (in which the halogen atom is 1 to 3 halogen atoms which are selected from the group consisting of a fluorine atom, a chlorine atom, and a bromine atom, and which are the same or different), an optionally substituted phenoxy group (in which the substituent is a pyridazinyloxy group substituted with 1 to 3 substituents which are selected from the group consisting of a fluorine atom, a chlorine atom, a bromine atom, and a $C_1$-$C_3$ alkoxy group, and which are the same or different), or a $C_1$-$C_3$ alkylthio group, or the represented by the formula: —CH$_2$CH$_2$—, —CH$_2$CH$_2$CH$_2$—, —CH(CH$_3$)CH$_2$CH$_2$—, —CH$_2$CH$_2$CH$_2$CH$_2$—, —CH=CH—CH=CH—, —OCH$_2$CH$_2$—, —OCH=CH—, —OCH=C(CH$_3$)—, —SCH=CH—, —N=CH—CH=CH—, —OCH$_2$O—, —OCH$_2$CH$_2$O—,

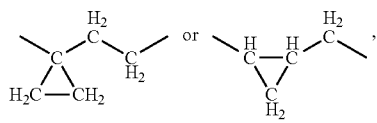

(2b) $R^2$ is more preferably an optionally substituted phenyl group represented by the general formula (II), wherein, in the general formula (II), each of $R^3$, $R^4$, $R^5$, $R^6$, and $R^7$ is independently a hydrogen atom, a fluorine atom, a chlorine atom, a bromine atom, an iodine atom, an optionally substituted $C_1$-$C_4$ alkyl group (in which the substituent is 1 to 3 fluorine atoms, or a $C_3$-$C_4$ cycloalkyl group, or a $C_1$-$C_3$ alkylthio group), a $C_2$-$C_3$ alkenyl group, a $C_2$-$C_3$ alkynyl group, an optionally substituted $C_3$-$C_5$ cycloalkyl group (in which the substituent is 1 to 3 substituents which are selected from the group consisting of a fluorine atom, a chlorine atom, a $C_1$-$C_3$ alkyl group, a $C_3$-$C_4$ cycloalkyl group, a $C_1$-$C_3$ alkoxy group, and a $C_1$-$C_3$ alkylthio group, and which are the same or different), a $C_6$-$C_7$ bicycloalkyl group, an optionally substituted phenyl group {in which the substituent is a fluorine atom, a chlorine atom, a bromine atom, a $C_1$-$C_3$ alkyl group, or a $C_1$-$C_3$ haloalkyl group (in which the halogen atom is 1 to 3 fluorine atoms)}, an optionally substituted 5- or 6-membered heterocyclic group {in which the heterocycle contains in the ring thereof one of a nitrogen atom, an oxygen atom, or a sulfur atom and optionally further contains 1 to 2 nitrogen atoms, and the substituent is 1 to 2 substituents which are selected from the group consisting of a fluorine atom, a chlorine atom, a bromine atom, a $C_1$-$C_3$ alkyl group, and a $C_1$-$C_3$ haloalkyl group (in which the halogen atom is 1 to 3 fluorine atoms), and which are the same or different}, a nitro group, a $C_1$-$C_3$ alkoxy group, a $C_1$-$C_3$ haloalkoxy group (in which the halogen atom is 1 to 3 fluorine atoms), an optionally substituted phenoxy group (in which the substituent is a pyridazinyloxy group substituted with 1 to 2 substituents which are selected from the group consisting of a fluorine atom, a chlorine atom, a bromine atom, and a $C_1$-$C_3$ alkoxy group, and which are the same or different), or a $C_1$-$C_3$ alkylthio group, or the group which the adjacent two of $R^3$, $R^4$, $R^5$, $R^6$, and $R^7$ taken together form is a group represented by the formula: —CH$_2$CH$_2$—, —CH$_2$CH$_2$CH$_2$—, —CH(CH$_3$)CH$_2$CH$_2$—, —CH$_2$CH$_2$CH$_2$CH$_2$—, —CH=CH—CH=CH—, —OCH$_2$CH$_2$—, —OCH=CH—, —OCH=C(CH$_3$)—, —SCH=CH—, —N=CH—CH=CH—, —OCH$_2$O—, —OCH$_2$CH$_2$O—,

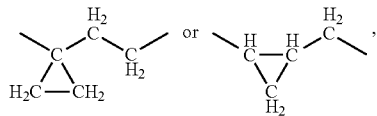

(2c) $R^2$ is further more preferably an optionally substituted phenyl group represented by the general formula (II), wherein, in the general formula (II), each of $R^3$, $R^4$, $R^5$, $R^6$, and $R^7$ is independently a hydrogen atom, a fluorine atom, a chlorine atom, a bromine atom, an iodine atom, a $C_1$-$C_4$ alkyl group, or a $C_3$-$C_5$ cycloalkyl group, or the group which the adjacent two of $R^3$, $R^4$, $R^5$, $R^6$, and $R^7$ taken together form is a group represented by the formula: —$CH_2CH_2CH_2$—, (2d) $R^2$ is still further more preferably an optionally substituted phenyl group represented by the general formula (II), wherein, in the general formula (II), each of $R^3$, $R^4$, $R^5$, $R^6$, and $R^7$ is independently a hydrogen atom, a fluorine atom, a chlorine atom, a bromine atom, an iodine atom, a $C_1$-$C_4$ alkyl group, or a $C_3$-$C_5$ cycloalkyl group, (2e) $R^2$ is especially preferably an optionally substituted phenyl group represented by the general formula (II), wherein, in the general formula (II), each of $R^3$, $R^4$, $R^5$, $R^6$, and $R^7$ is independently a hydrogen atom, a methyl group, or a cyclopropyl group, (2f) $R^2$ is most preferably a 2-cyclopropyl-6-methylphenyl group, (3a) $L^1$ is preferably a halogen atom, (3b) $L^1$ is more preferably a chlorine atom or a bromine atom, (3c) $L^1$ is further more preferably a chlorine atom.

In the compound (III) in the present invention, (4a) $L^2$ is preferably a halogen atom, (4b) $L^2$ is more preferably a chlorine atom, a bromine atom, or an iodine atom, (4c) $L^2$ is most preferably a chlorine atom.

In the compound (IV) in the present invention, M is a hydrogen atom or an alkali metal, (5a) M is preferably a hydrogen atom, sodium, or potassium, (5b) M is more preferably a hydrogen atom or sodium.

The compound (I) obtained from the combination of $R^1$ being (1a), $R^2$ being selected from (2a) to (2f), and $L^1$ being selected from (3a) to (3c) is also preferred. Further, the compound (III) obtained from the combination of $R^1$ being (1a), $L^1$ being selected from (3a) to (3c), and $L^2$ being selected from (4a) to (4c) is also preferred. The compound (IV) obtained from the combination of $R^2$ being selected from (2a) to (20 and M being selected from (5a) and (5b) is also preferred.

In the method of the present invention, the reaction can be conducted in the presence or absence of a base.

In the method of the present invention, the base used in the reaction is, for example, a metal hydroxide, a metal carbonate, a metal hydrogencarbonate, a metal alkoxide, an organic acid metal salt, a metal hydride, a metal, an amine, or an organometallic base.

In the present invention, the "metal hydroxide" is a hydroxide of an arbitrary metal, and can be, for example, an alkali metal hydroxide, an alkaline earth metal hydroxide, aluminum hydroxide, iron hydroxide, or zinc hydroxide, and is preferably lithium hydroxide, sodium hydroxide, potassium hydroxide, rubidium hydroxide, cesium hydroxide, beryllium hydroxide, magnesium hydroxide, calcium hydroxide, strontium hydroxide, barium hydroxide, aluminum hydroxide, iron hydroxide, or zinc hydroxide, more preferably lithium hydroxide, sodium hydroxide, potassium hydroxide, or cesium hydroxide, further more preferably sodium hydroxide or potassium hydroxide, most preferably sodium hydroxide.

In the present invention, the "metal carbonate" is a carbonate of an arbitrary metal, and can be, for example, an alkali metal carbonate or an alkaline earth metal carbonate, and is preferably lithium carbonate, sodium carbonate, potassium carbonate, rubidium carbonate, cesium carbonate, beryllium carbonate, magnesium carbonate, calcium carbonate, strontium carbonate, or barium carbonate, more preferably sodium carbonate or potassium carbonate, most preferably potassium carbonate.

In the present invention, the "metal hydrogencarbonate" is a hydrogencarbonate of an arbitrary metal, and can be, for example, an alkali metal hydrogencarbonate, and is preferably sodium hydrogencarbonate or potassium hydrogencarbonate.

In the present invention, the "metal alkoxide" is a compound comprising an alcohol having an arbitrary metal bonded thereto, and can be, for example, an alkali metal alkoxide or an alkaline earth metal alkoxide, and is preferably lithium methoxide, lithium ethoxide, lithium t-butoxide, lithium t-amyloxide, lithium phenoxide, lithium 2-t-butylphenoxide, lithium 2,6-di-t-butylphenoxide, lithium 2,6-di-t-butyl-4-methylphenoxide, sodium methoxide, sodium ethoxide, sodium t-butoxide, sodium t-amyloxide, sodium phenoxide, sodium 2-t-butylphenoxide, sodium 2,6-di-t-butylphenoxide, sodium 2,6-di-t-butyl-4-methylphenoxide, potassium methoxide, potassium ethoxide, potassium t-butoxide, potassium t-amyloxide, potassium phenoxide, potassium 2-t-butylphenoxide, potassium 2,6-di-t-butylphenoxide, potassium 2,6-di-t-butyl-4-methylphenoxide, rubidium t-butoxide, cesium t-butoxide, beryllium di(t-butoxide), magnesium di(t-butoxide), calcium di(t-butoxide), strontium di(t-butoxide), or barium di(t-butoxide), more preferably lithium methoxide, lithium ethoxide, lithium t-butoxide, lithium t-amyloxide, lithium 2,6-di-t-butylphenoxide, lithium 2,6-di-t-butyl-4-methylphenoxide, sodium methoxide, sodium ethoxide, sodium t-butoxide, sodium t-amyloxide, sodium 2,6-di-t-butylphenoxide, sodium 2,6-di-t-butyl-4-methylphenoxide, potassium methoxide, potassium ethoxide, potassium t-butoxide, potassium t-amyloxide, potassium 2,6-di-t-butylphenoxide, potassium 2,6-di-t-butyl-4-methylphenoxide, rubidium t-butoxide, or cesium t-butoxide, further more preferably sodium methoxide, sodium ethoxide, sodium t-butoxide, or potassium t-butoxide, most preferably sodium t-butoxide or potassium t-butoxide.

In the present invention, the "organic acid metal salt" is a compound comprising an organic acid having an arbitrary metal bonded thereto, and can be, for example, an organic acid alkali metal salt or an organic acid alkaline earth metal salt, and is preferably lithium formate, lithium acetate, sodium formate, sodium acetate, sodium benzoate, potassium formate, potassium acetate, potassium benzoate, rubidium acetate, cesium acetate, beryllium acetate, magnesium acetate, calcium acetate, strontium acetate, or barium acetate, more preferably sodium formate, sodium acetate, potassium formate, or potassium acetate, further more preferably sodium formate or sodium acetate.

In the present invention, the "metal hydride" is a hydride of an arbitrary metal, and can be, for example, an alkali metal hydride or an alkaline earth metal hydride, and is preferably lithium hydride, sodium hydride, potassium hydride, strontium hydride, cesium hydride, beryllium hydride, magnesium hydride, calcium hydride, strontium hydride, or barium hydride, more preferably lithium hydride, sodium hydride, or potassium hydride, further more preferably sodium hydride.

In the present invention, the "metal" is an arbitrary metal, and can be, for example, lithium, boron, sodium, magnesium, aluminum, potassium, calcium, titanium, chromium, manganese, nickel, copper, zinc, a zinc-copper alloy, silver, tin, tellurium, mercury, a lithium-mercury alloy, cerium, europium, or ytterbium, and is preferably an alkali metal or an alkaline earth metal, more preferably lithium, sodium, potassium, rubidium, cesium, beryllium, magnesium, calcium, strontium, or barium, further more preferably lithium, sodium, or potassium, most preferably sodium or potassium.

In the present invention, the "amine" is a basic compound having nitrogen, and can be, for example, an aliphatic tertiary amine, an alicyclic tertiary amine, an aromatic tertiary amine, pyridines, or a metal amide, and is preferably trimethylamine, triethylamine, tripropylamine, diisopropylamine, triisopropylamine, tributylamine, diisopropylethylamine, N-methylmorpholine, 1,4-diazabicyclo[2.2.2]octane (DABCO), 1,8-diazabicyclo[5.4.0]undec-7-ene (DBU), dimethylaniline, diethylaniline, pyridine, lutidine, collidine, 4-(N,N-dimethylamino)pyridine, lithium amide, sodium amide, potassium amide, lithium diethylamide, lithium diisopropylamide, lithium cyclohexylisopropylamide, lithium tetramethylpiperazide, lithium bis(trimethylsilyl)amide, sodium bis(trimethylsilyl)amide, or potassium bis(trimethylsilyl)amide, more preferably lithium amide, sodium amide, potassium amide, lithium diethylamide, lithium diisopropylamide, lithium cyclohexylisopropylamide, lithium tetramethylpiperazide, lithium bis(trimethylsilyl)amide, sodium bis(trimethylsilyl)amide, or potassium bis(trimethylsilyl)amide, further more preferably sodium amide, potassium amide, sodium bis(trimethylsilyl)amide, or potassium bis(trimethylsilyl)amide, most preferably sodium amide or potassium amide.

In the present invention, the "organometallic base" is a compound comprising an arbitrary metal and a carbon atom bonded thereto, and can be, for example, methyllithium, n-butyllithium, s-butyllithium, t-butyllithium, phenyllithium, sodium naphthalene, potassium naphthalene, potassium diphenylethylene, benzylpotassium, cumylpotassium, methylmagnesium chloride, methylmagnesium bromide, methylmagnesium iodide, t-butylmagnesium chloride, t-butylmagnesium bromide, phenylmagnesium chloride, phenylmagnesium bromide, or cumylcesium, and is preferably methyllithium, n-butyllithium, s-butyllithium, t-butyllithium, phenyllithium, sodium naphthalene, potassium naphthalene, potassium diphenylethylene, benzylpotassium, cumylpotassium, or cumylcesium, more preferably t-butyllithium, sodium naphthalene, or potassium naphthalene.

The base used is preferably an alkali metal hydroxide, an alkaline earth metal hydroxide, an alkali metal carbonate, an alkaline earth metal carbonate, an alkali metal hydrogencarbonate, an alkali metal alkoxide, an alkaline earth metal alkoxide, an organic acid alkali metal salt, an organic acid alkaline earth metal salt, an alkali metal hydride, an alkaline earth metal hydride, an alkali metal, an alkaline earth metal, an aliphatic tertiary amine, an alicyclic tertiary amine, an aromatic tertiary amine, pyridines, a metal amide, or an organometallic base, more preferably lithium hydroxide, sodium hydroxide, potassium hydroxide, cesium hydroxide; lithium methoxide, lithium ethoxide, lithium t-butoxide, lithium t-amyloxide, lithium 2,6-di-t-butylphenoxide, lithium 2,6-di-t-butyl-4-methylphenoxide, sodium methoxide, sodium ethoxide, sodium t-butoxide, sodium t-amyloxide, sodium 2,6-di-t-butylphenoxide, sodium 2,6-di-t-butyl-4-methylphenoxide, potassium methoxide, potassium ethoxide, potassium t-butoxide, potassium t-amyloxide, potassium 2,6-di-t-butylphenoxide, potassium 2,6-di-t-butyl-4-methylphenoxide, rubidium t-butoxide, cesium t-butoxide; lithium hydride, sodium hydride, potassium hydride; lithium, sodium, potassium; lithium amide, sodium amide, potassium amide, lithium diethylamide, lithium diisopropylamide, lithium cyclohexylisopropylamide, lithium tetramethylpiperazide, lithium bis(trimethylsilyl)amide, sodium bis(trimethylsilyl)amide, potassium bis(trimethylsilyl)amide; or methyllithium, n-butyllithium, s-butyllithium, t-butyllithium, phenyllithium, sodium naphthalene, potassium naphthalene, potassium diphenylethylene, benzylpotassium, cumylpotassium, or cumylcesium, further more preferably sodium hydroxide, potassium hydroxide; sodium methoxide, sodium ethoxide, sodium t-butoxide, potassium t-butoxide; sodium hydride, potassium hydride; sodium, potassium; or sodium amide, potassium amide, sodium bis(trimethylsilyl)amide, or potassium bis(trimethylsilyl)amide, still further more preferably sodium hydroxide, potassium hydroxide; sodium t-butoxide, potassium t-butoxide; sodium hydride, potassium hydride; or sodium amide, or potassium amide, most preferably sodium hydroxide, potassium hydroxide; or sodium t-butoxide, or potassium t-butoxide.

In the present invention, preferably, when M is an alkali metal, the reaction between the compound represented by the general formula (III) and the compound represented by the general formula (IV) can be conducted in the absence of a base.

In the method of the present invention, the reaction can be conducted in the presence or absence of a solvent.

The solvent used in the reaction can be water; an alcohol, such as methanol, ethanol, isopropanol, t-butanol, 2-methyl-4-phenylbutanol, 1-octanol, 2-octanol, 2-ethyl-1-hexanol, cyclohexanol, 2-methylcyclohexanol, or hexylene glycol; a ketone, such as acetone, methyl isobutyl ketone, acetophenone, cyclohexanone, or benzophenone; a nitrile, such as acetonitrile, benzonitrile, or orthotolunitrile; an ester, such as ethyl acetate, butyl acetate, methyl benzoate, or t-butyl benzoate; a hydrocarbon, such as hexane, heptane, octane, decane, undecane, dodecane, cyclohexane, or decalin; a hydrocarbon halide, such as methylene chloride, chloroform, or dichloroethane; an ether, such as diethyl ether, tetrahydrofuran, dioxane, 3-methoxytoluene, 1,2-dimethoxybenzene, ethyl phenyl ether, or diphenyl ether; an aromatic hydrocarbon, such as toluene, xylene, or butylbenzene; an aromatic hydrocarbon halide, such as chlorobenzene or o-dichlorobenzene; an amide, such as dimethylformamide, dimethylacetamide, N-methylpyrrolidinone, or 1,3-dimethyl-2-imidazolidinone; pyridines, such as pyridine, lutidine, collidine, or quinoline; a sulfoxide, such as dimethylsulfoxide; sulfolane; an aliphatic amine, such as triethylamine, tributylamine, or diisopropylethylamine; an aromatic amine, such as dimethylaniline or diisopropylaniline; or a mixed solvent thereof, and is preferably methanol, ethanol, isopropanol, t-butanol, 2-methyl-4-phenylbutanol, 1-octanol, 2-octanol, 2-ethyl-1-hexanol, cyclohexanol, 2-methylcyclohexanol, hexylene glycol; acetone, methyl isobutyl ketone, acetophenone, benzophenone; acetonitrile, benzonitrile, orthotolunitrile; ethyl acetate, butyl acetate, methyl benzoate, t-butyl benzoate; hexane, heptane, octane, decane, undecane, dodecane, cyclohexane, decalin; methylene chloride, chloroform, dichloroethane; diethyl ether, tetrahydrofuran, dioxane, 3-methoxytoluene, 1,2-dimethoxybenzene, ethyl phenyl ether, diphenyl ether; toluene, xylene, butylbenzene; chlorobenzene, o-dichlorobenzene; dimethylformamide, dimethylacetamide, N-methylpyrrolidinone, 1,3-dimethyl-2-imidazolidinone; pyridine, lutidine, collidine, quinoline; dimethyl sulfoxide, sulfolane; triethylamine, tributylamine, diisopropylethylamine; dimethylaniline, diisopropylaniline; or a mixed solvent, more preferably methanol, ethanol, isopropanol, t-butanol, 2-methyl-4-phenylbutanol, 1-octanol, 2-octanol, 2-ethyl-1-hexanol, cyclohexanol, 2-methylcyclohexanol, or hexylene glycol; benzophenone, cyclohexanone; benzonitrile, orthotolunitrile; decane, undecane, decalin; 3-methoxytoluene, 1,2-dimethoxybenzene, ethyl phenyl ether, diphenyl ether; o-dichlorobenzene; N-methylpyrrolidinone, 1,3-dimethyl-2-imidazolidinone; quinoline; sulfolane, dimethyl sulfoxide; tributylamine; dimethylaniline, diisopropylaniline; or a mixed solvent thereof, further more preferably t-butanol, 2-methyl-4-phenylbutanol, 1-octanol, 2-octanol, 2-ethyl-1-hexanol, cyclohexanol, 2-methylcyclohexanol, or hexylene glycol; benzophenone; benzonitrile, orthotolunitrile; decane, undecane, decalin; 3-methoxytoluene, ethyl phenyl ether, diphenyl ether; o-dichlorobenzene; quinoline; tributylamine; dimethylaniline, diisopropylaniline; or a mixed solvent thereof, especially preferably t-butanol, 2-methyl-4-phenylbutanol, 2-octanol, cyclohexanol, 2-methylcyclohexanol, 3-methoxytoluene, ethyl phenyl ether, o-dichlorobenzene; dimethylaniline; or a mixed solvent thereof, most preferably t-butanol.

In the reaction in the present invention, a reaction promoter can be added if necessary.

The reaction promoter can be, for example, the above-mentioned solvent; polyethylene glycol; or a quaternary ammonium salt, such as tetrabutylammonium chloride, tetrabutylammonium bromide, tetraethylammonium chloride, tetraethylammonium bromide, benzyltriethylammonium chloride, benzyltriethylammonium bromide, benzyltributylammonium chloride, or benzyltributylammonium bromide, and is preferably water; methanol, ethanol, isopropanol, t-butanol; acetonitrile; tetrahydrofuran, dioxane; dimethylformamide, dimethylacetamide, 1,3-dimethyl-2-imidazolidinone; dimethyl sulfoxide; polyethylene glycol; tetrabutylammonium bromide, tetraethylammonium bromide; or a mixture thereof, more preferably water; isopropanol, t-butanol; dioxane; or a mixture thereof.

The amount of the compound represented by the general formula (IV) used in the present invention is, relative to 1 mol of the compound represented by the general formula (III), generally 1 to 10 mol, preferably 3 to 10 mol, more preferably 3 to 5 mol. By adding the compound represented by the general formula (IV) in an excess amount to the compound represented by the general formula (III), a 3-(substituted oxy)-4-pyridazinol derivative (I) can be obtained with higher selectivity and in higher yield.

The amount of the base used in the present invention is, relative to 1 mol of the compound represented by the general formula (IV), generally 1 to 10 mol, preferably 1 to 5 mol, more preferably 3 to 5 mol.

The amount of the reaction solvent used in the present invention is generally 1 to 100 times (%), preferably 5 to 50 times (%), more preferably 5 to 30 times (%) the weight (g) of the compound represented by the general formula (III).

The reaction substrate concentration (% by weight) of the compound represented by the general formula (III) in the present invention is generally 0.1 to 50% by weight, preferably 1 to 25% by weight, more preferably 1 to 10% by weight.

In the present invention, a method for addition of the compound represented by the general formula (III) can be, for example, addition in one operation, batchwise addition, or dropwise addition. In the batchwise addition or dropwise addition, the compound can be used in a dispersed or dissolved form in a solvent. With respect to the solvent used, there is no particular limitation as long as it does not adversely affect the reaction, and the solvent can be, for example, an alcohol, a hydrocarbon, a hydrocarbon halide, an ether, or a mixed solvent thereof, and is preferably t-butanol, toluene, o-dichlorobenzene, tetrahydrofuran, or 1,4-dioxane, more preferably t-butanol, o-dichlorobenzene, or 1,4-dioxane, most preferably t-butanol.

The addition time is generally 0 minute to 30 hours, preferably 0 minute to 20 hours, more preferably 0 to 10 hours.

The reaction temperature in the present invention is generally 0° C. to 300° C., preferably 100° C. to 230° C., more preferably 100° C. to 190° C.

The reaction time in the present invention is generally 30 minutes to 50 hours, preferably 1 to 20 hours.

An after-treatment step is described below.

In the present invention, the compound represented by the general formula (I) and obtained by a reaction between the compound represented by the general formula (III) and the compound represented by the general formula (IV), or the reaction mixture containing the compound(s) represented by the general formula (III) or/and (IV), or a salt thereof can be isolated or purified by a known method, for example, concentration, concentration under reduced pressure, distillation, fractional distillation, extraction with a solvent (including extraction of an aqueous mixture under acidic or alkaline conditions with an organic solvent), washing with a solvent, crystallization, recrystallization, adsorption, or chromatography.

When excess of the compound represented by the general formula (IV) is used in the reaction, the remaining compound can be isolated or purified by a known method, for example, concentration, concentration under reduced pressure, distillation, fractional distillation, extraction with a solvent (including extraction of an aqueous mixture under acidic or alkaline conditions with an organic solvent), washing with a solvent, crystallization, recrystallization, adsorption, or chromatography.

The compound represented by the general formula (III) used in the present invention is a known compound, or can be easily prepared by a known method {for example, a method described in Helvetica Chimica Acta, vol. 39, pp. 1,755 to 1,762 (1956) or Japanese Unexamined Patent Publication No. 2004-2263} or a method according thereto.

The compound represented by the general formula (IV) used in the present invention is a known compound, or can be easily prepared by a known method (for example, a method described in Japanese Unexamined Patent Publication No. 2004-2263) or a method according thereto.

Further, the present invention is directed to a method for producing a 3-(substituted oxy)-4-pyridazinyl 4-morpholinecarboxylate by using the above-obtained 3-(substituted oxy)-4-pyridazinol derivative (I). Specifically, the present invention is directed to a method for producing a 3-(substituted oxy)-4-pyridazinyl 4-morpholinecarboxylate represented by the following general formula (V):

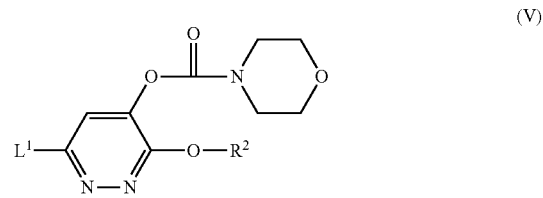

(V)

wherein $R^2$ and $L^1$ are as defined above, the method comprising:

in accordance with the above-mentioned method, obtaining a compound represented by the following general formula (I):

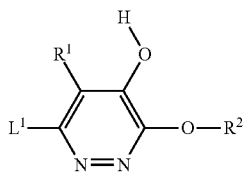

(I)

wherein R$^1$, R$^2$, and L$^1$ are as defined above,
and
reacting the obtained compound represented by the general formula (I) with a compound represented by the following general formula (VI):

(VI)

wherein X is a chlorine atom, a bromine atom, or an iodine atom, preferably a chlorine atom
in the presence of a base and in the presence or absence of a solvent to produce a 3-(substituted oxy)-4-pyridazinyl 4-morpholinecarboxylate represented by the general formula (V).

The amount of the compound represented by the general formula (VI) used in this reaction is, relative to 1 mol of the compound represented by the general formula (I), generally 0.5 to 10 mol, preferably 1 to 5 mol, more preferably 1 to 3 mol.

With respect to the base used in the reaction between the compound (I) and compound (VI), any base may be used as long as it does not inhibit the reaction, and, for example, a base the same as used in the reaction between the compound (III) and the compound (IV) can be used. The base is preferably a metal carbonate or an amine, more preferably potassium carbonate or triethylamine. The amount of the base used in the above reaction is, relative to 1 mol of the compound represented by the general formula (V), generally 0.5 to 20 mol, preferably 1 to 5 mol, more preferably 1 to 3 mol.

The above reaction can be conducted in the presence or absence of a solvent. With respect to the solvent used in the reaction between the compound (I) and the compound (VI), any solvent may be used as long as it does not inhibit the reaction, and, for example, a solvent the same as used in the reaction between the compound (III) and the compound (IV) can be used. The solvent is preferably a ketone, an ester, or an aromatic hydrocarbon, more preferably acetone, methyl isobutyl ketone, butyl acetate, or toluene. The amount of the reaction solvent used in the above reaction is generally 1 to 100 times (%), preferably 5 to 50 times (%), more preferably 5 to 30 times (%) the weight (g) of the compound represented by the general formula (I).

The reaction temperature in the above reaction varies depending mainly on the raw material compounds, reaction reagent, and type of the solvent used, but is generally −90 to 200° C., preferably 0 to 100° C., more preferably 30 to 70° C.

The reaction time in the above reaction varies depending mainly on the reaction temperature, raw material compounds, reaction reagent, and type of the solvent used, but is generally 30 minutes to 50 hours, preferably 1 hour to 20 hours.

With respect to the after-treatment step, an after-treatment similar to the after-treatment step for the reaction between the compound represented by the general formula (III) and the compound represented by the general formula (IV) can be performed.

EXAMPLES

In the method of present invention, quantitative determination was made by an HPLC internal standard analysis method. Conditions for HPLC analysis are as follows: HPLC column: L-Column ODS φ4.6×250 mm (Chemicals Evaluation and Research Institute, Japan); mobile phase: 20 mM aqueous phosphoric acid solution:acetonitrile=60:40 (vol %); flow rate: 1.0 mL/min; detection wavelength: 274 nm, injection amount: 1 µL; and standard reagent: 3-methoxytoluene.

Example 1

Production of 6-chloro-3-(2-cyclopropyl-6-methylphenoxy)-4-pyridazinol

To a mixture of 13.0 g (87.0 mmol) of 2-cyclopropyl-6-methylphenol and 1,2-dichlorobenzene (78.3 mL) was added 3.67 g (87.0 mmol) of 95% sodium hydroxide at room temperature. The resultant mixture was heated to 180° C. and subjected to azeotropic dehydration under reflux while stirring for 30 minutes. To the resultant solution was added dropwise the preliminarily prepared solution of 5.00 g (purity: 95.7%; 29.0 mmol) of 4-hydroxy-3,6-dichloropyridazine in t-butanol (95.0 g) at 180° C. over 5 hours. (The t-butanol was distilled off simultaneously with the dropwise addition of the solution.) After stirring at 180° C. for another 2 hours, the reaction mixture was cooled to room temperature, and 78.7 g of pure water was added to the cooled mixture and stirred for 30 minutes, and an organic phase containing 2-cyclopropyl-6-methylphenol added in an excess amount was separated. 50.0 g of toluene was added to the resultant aqueous phase and stirred at room temperature for 30 minutes, and an organic phase containing 2-cyclopropyl-6-methylphenol was separated. This operation was repeated twice. Then, the resultant aqueous phase containing a sodium salt of 6-chloro-3-(2-cyclopropyl-6-methylphenoxy)-4-pyridazinol was added dropwise to a 4% aqueous hydrochloric acid solution at 0° C. to deposit solids, followed by filtration. The resultant solids were washed with pure water and dried under a reduced pressure, and dissolved in an organic solvent and quantitatively determined by an HPLC internal standard analysis method, which showed that 8.30 g of 6-chloro-3-(2-cyclopropyl-6-methylphenoxy)-4-pyridazinol (purity: 90.9%; yield: 94%) and 29 mg of 3-chloro-6-(2-cyclopropyl-6-methylphenoxy)-4-pyridazinol (yield: 0.4%) were obtained.

Example 2

Production of 6-chloro-3-(2-cyclopropyl-6-methylphenoxy)-4-pyridazinol

To a mixture of 13.0 g (87.0 mmol) of 2-cyclopropyl-6-methylphenol and 1,2-dichlorobenzene (78.3 mL) was added 3.67 g (87.0 mmol) of 95% sodium hydroxide at room temperature. The resultant mixture was heated to 180° C. and subjected to azeotropic dehydration under reflux while stirring for 30 minutes. To the resultant solution was added dropwise the preliminarily prepared solution of 5.00 g (purity: 95.7%; 29.0 mmol) of 4-hydroxy-3,6-dichloropyridazine in t-butanol (95.0 g) at 180° C. over 10 hours. (The t-butanol was distilled off simultaneously with the dropwise addition of the solution.) After stirring at 180° C. for another 30 minutes, the reaction mixture was cooled to room temperature, and 78.7 g of pure water was added to the cooled mixture and stirred for 30 minutes, and an organic phase containing 2-cyclopropyl-6-methylphenol added in an excess amount was separated. 50.0 g of toluene was added to the resultant aqueous phase and stirred at room temperature for 30 minutes, and an organic phase containing 2-cyclopropyl-6-methylphenol was separated. This operation was repeated twice. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 6.73 g of 6-chloro-3-(2-cyclopropyl-6-methylphenoxy)-4-pyridazinol (yield: 84%) and 27 mg of 3-chloro-6-(2-cyclopropyl-6-methylphenoxy)-4-pyridazinol (yield: 0.4%) were obtained.

Example 3

Production of 6-chloro-3-(2-cyclopropyl-6-methylphenoxy)-4-pyridazinol

To a mixture of 12.8 g (86.4 mmol) of 2-cyclopropyl-6-methylphenol and 1,2-dichlorobenzene (78.3 mL) was added 3.64 g (86.4 mmol) of 95% sodium hydroxide at room temperature. The resultant mixture was heated to 180° C. and subjected to azeotropic dehydration under reflux while stirring for 30 minutes. To the resultant solution was added dropwise the preliminarily prepared solution of 5.00 g (purity: 95%; 28.8 mmol) of 4-hydroxy-3,6-dichloropyridazine in t-butanol (95.0 g) at 180° C. over 2 hours. (The t-butanol was distilled off simultaneously with the dropwise addition of the solution.) After stirring at 180° C. for another 30 minutes, the reaction mixture was cooled to room temperature, and 78.7 g of pure water was added to the cooled mixture and stirred for 30 minutes, and an organic phase containing 2-cyclopropyl-6-methylphenol added in an excess amount was separated. 50.0 g of toluene was added to the resultant aqueous phase and stirred at room temperature for 30 minutes, and an organic phase containing 2-cyclopropyl-6-methylphenol was separated. This operation was repeated twice. Then, the resultant aqueous phase containing a sodium salt of 6-chloro-3-(2-cyclopropyl-6-methylphenoxy)-4-pyridazinol was added dropwise to a 4% aqueous hydrochloric acid solution at 0° C. to deposit solids, followed by filtration. The resultant solids were washed with pure water and dried under a reduced pressure, and dissolved in an organic solvent and quantitatively determined by an HPLC internal standard analysis method, which showed that 7.17 g of 6-chloro-3-(2-cyclopropyl-6-methylphenoxy)-4-pyridazinol (yield: 91%) and 43 mg of 3-chloro-6-(2-cyclopropyl-6-methylphenoxy)-4-pyridazinol (yield: 0.6%) were obtained.

Example 4

Production of 6-chloro-3-(2-cyclopropyl-6-methylphenoxy)-4-pyridazinol

To a mixture of 12.8 g (86.4 mmol) of 2-cyclopropyl-6-methylphenol and 1,2-dichlorobenzene (78.3 mL) was added 5.09 g (86.4 mmol) of 95% potassium hydroxide at room temperature. The resultant mixture was heated to 180° C. and subjected to azeotropic dehydration under reflux while stirring for 30 minutes. To the resultant solution was added dropwise the preliminarily prepared solution of 5.00 g (purity: 95.0%; 28.8 mmol) of 4-hydroxy-3,6-dichloropyridazine in t-butanol (95.0 g) at 180° C. over 2 hours. (The t-butanol was distilled off simultaneously with the dropwise addition of the solution.) After stirring at 180° C. for another 2 hours, the reaction mixture was cooled to room temperature, and 78.7 g of pure water was added to the cooled mixture and stirred for 30 minutes, and an organic phase containing 2-cyclopropyl-6-methylphenol added in an excess amount was separated. 50.0 g of toluene was added to the resultant aqueous phase and stirred at room temperature for 30 minutes, and an organic phase containing 2-cyclopropyl-6-methylphenol was separated. This operation was repeated twice. Then, the resultant aqueous phase containing a potassium salt of 6-chloro-3-(2-cyclopropyl-6-methylphenoxy)-4-pyridazinol was added dropwise to a 4% aqueous hydrochloric acid solution at 0° C. to deposit solids, followed by filtration. The resultant solids were washed with pure water and dried under a reduced pressure, and dissolved in an organic solvent and quantitatively determined by an HPLC internal standard analysis method, which showed that 8.30 g of 6-chloro-3-(2-cyclopropyl-6-methylphenoxy)-4-pyridazinol (purity: 90.4%; yield: 90%) and 69 mg of 3-chloro-6-(2-cyclopropyl-6-methylphenoxy)-4-pyridazinol (yield: 0.9%) were obtained.

Example 5

Production of 6-chloro-3-(2-cyclopropyl-6-methylphenoxy)-4-pyridazinol

To a mixture of 12.8 g (86.4 mmol) of 2-cyclopropyl-6-methylphenol and 1,2-dichlorobenzene (78.3 mL) was added 15.3 g (86.4 mmol) of 95% cesium hydroxide at room temperature. The resultant mixture was heated to 180° C. and subjected to azeotropic dehydration under reflux while stirring for 30 minutes. To the resultant solution was added dropwise the preliminarily prepared solution of 5.00 g (purity: 95.0%; 28.8 mmol) of 4-hydroxy-3,6-dichloropyridazine in t-butanol (95.0 g) at 180° C. over 2 hours. (The t-butanol was distilled off simultaneously with the dropwise addition of the solution.) After stirring at 180° C. for another 2 hours, the reaction mixture was cooled to room temperature, and 100 g of pure water was added to the cooled mixture and stirred for 30 minutes, and an organic phase containing 2-cyclopropyl-6-methylphenol added in an excess amount was separated. 50.0 g of toluene was added to the resultant aqueous phase and stirred at room temperature for 30 minutes, and an organic phase containing 2-cyclopropyl-6-methylphenol was separated. This operation was repeated twice. Then, the resultant aqueous phase containing a cesium salt of 6-chloro-3-(2-cyclopropyl-6-methylphenoxy)-4-pyridazinol was added dropwise to a 4% aqueous hydrochloric acid solution at 0° C. to deposit solids, followed by filtration. The resultant solids were washed with pure water and dried under a reduced pressure, and dissolved in an organic solvent and quantitatively determined by an HPLC internal standard analysis method, which showed that 7.92 g of 6-chloro-3-(2-cyclopropyl-6-methylphenoxy)-4-pyridazinol (purity: 76.1%; yield: 76%) and 166 mg of 3-chloro-6-(2-cyclopropyl-6-methylphenoxy)-4-pyridazinol (yield: 2.1%) were obtained.

Example 6

Production of 6-chloro-3-(2-cyclopropyl-6-methylphenoxy)-4-pyridazinol

To a mixture of 1.34 g (9.05 mmol) of 2-cyclopropyl-6-methylphenol and 1,2-dichlorobenzene (7.00 mL) was added 1.20 g (9.05 mmol) of 85% potassium t-butoxide at room temperature. The resultant mixture was heated to 180° C. and subjected to azeotropic dehydration under reflux while stirring for 30 minutes. To the resultant solution was added dropwise the preliminarily prepared solution of 4.97 g (purity: 96.0%; 2.89 mmol) of 4-hydroxy-3,6-dichloropyridazine in t-butanol (35.0 g) at 170° C. over 2 hours. (The t-butanol was distilled off simultaneously with the dropwise addition of the solution.) After stirring at 180° C. for another 2 hours, the reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 701 mg of 6-chloro-3-(2-cyclopropyl-6-methylphenoxy)-4-pyridazinol (yield: 88%) and 6.9 mg of 3-chloro-6-(2-cyclopropyl-6-methylphenoxy)-4-pyridazinol (yield: 0.9%) were obtained.

Example 7

Production of 6-chloro-3-(2-cyclopropyl-6-methylphenoxy)-4-pyridazinol

To a mixture of 12.9 g (87.0 mmol) of 2-cyclopropyl-6-methylphenol and 1,2-dichlorobenzene (78.3 mL) was added 3.67 g (87.0 mmol) of 95% sodium hydroxide at room temperature. The resultant mixture was heated to 180° C. and subjected to azeotropic dehydration under reflux while stirring for 30 minutes. To the resultant solution was added dropwise the preliminarily prepared solution of 4.97 g (purity: 95.7%; 29.0 mmol) of 4-hydroxy-3,6-dichloropyridazine in t-butanol (95.0 g) at 160° C. over 9 hours. (The t-butanol was distilled off simultaneously with the dropwise addition of the solution.) After stirring at 180° C. for another 30 minutes, the reaction mixture was cooled to room temperature, and 78.7 g of pure water was added to the cooled mixture and stirred for 30 minutes, and an organic phase containing 2-cyclopropyl-6-methylphenol added in an excess amount was separated. 50.0 g of toluene was added to the resultant aqueous phase and stirred at room temperature for 30 minutes, and an organic phase containing 2-cyclopropyl-6-methylphenol was separated. This operation was repeated twice. Then, the resultant aqueous solution containing a sodium salt of 6-chloro-3-(2-cyclopropyl-6-methylphenoxy)-4-pyridazinol was quantitatively determined by an HPLC internal standard analysis method, which showed that 6.86 g of 6-chloro-3-(2-cyclopropyl-6-methylphenoxy)-4-pyridazinol (yield: 86%) and 29 mg of 3-chloro-6-(2-cyclopropyl-6-methylphenoxy)-4-pyridazinol (yield: 0.4%) were obtained.

Example 8

Production of 6-chloro-3-(2-cyclopropyl-6-methylphenoxy)-4-pyridazinol

To a mixture of 12.8 g (86.4 mmol) of 2-cyclopropyl-6-methylphenol and 1,2-dichlorobenzene (78.3 mL) was added 3.64 g (86.4 mmol) of 95% sodium hydroxide at room temperature. The resultant mixture was heated to 180° C. and subjected to azeotropic dehydration under reflux while stirring for 30 minutes. To the resultant solution was added dropwise the preliminarily prepared solution of 5.00 g (purity: 95%; 28.8 mmol) of 4-hydroxy-3,6-dichloropyridazine in t-butanol (95.0 g) at 160° C. over 2 hours. (The t-butanol was distilled off simultaneously with the dropwise addition of the solution.) After stirring at 180° C. for another 30 minutes, the reaction mixture was cooled to room temperature, and 78.7 g of pure water was added to the cooled mixture and stirred for 30 minutes, and an organic phase containing 2-cyclopropyl-6-methylphenol added in an excess amount was separated. 50.0 g of toluene was added to the resultant aqueous phase and stirred at room temperature for 30 minutes, and an organic phase containing 2-cyclopropyl-6-methylphenol was separated. This operation was repeated twice. Then, the resultant aqueous solution containing a sodium salt of 6-chloro-3-(2-cyclopropyl-6-methylphenoxy)-4-pyridazinol was quantitatively determined by an HPLC internal standard analysis method, which showed that 6.10 g of 6-chloro-3-(2-cyclopropyl-6-methylphenoxy)-4-pyridazinol (yield: 77%) and 39 mg of 3-chloro-6-(2-cyclopropyl-6-methylphenoxy)-4-pyridazinol (yield: 0.5%) were obtained.

Example 9

Production of 6-chloro-3-(2-cyclopropyl-6-methylphenoxy)-4-pyridazinol

To a mixture of 12.9 g (87.0 mmol) of 2-cyclopropyl-6-methylphenol and 1,2-dichlorobenzene (78.3 mL) was added 3.67 g (87.0 mmol) of 95% sodium hydroxide at room temperature. The resultant mixture was heated to 180° C. and subjected to azeotropic dehydration under reflux while stirring for 30 minutes. To the resultant solution was added dropwise the preliminarily prepared solution of 5.00 g (purity: 95.7%; 29.0 mmol) of 4-hydroxy-3,6-dichloropyridazine in t-butanol (95.0 g) at 160° C. over 5 hours. (The t-butanol was distilled off simultaneously with the dropwise addition of the solution.) After stirring at 180° C. for another 30 minutes, the reaction mixture was cooled to room temperature, and 78.7 g of pure water was added to the cooled mixture and stirred for 30 minutes, and an organic phase containing 2-cyclopropyl-6-methylphenol added in an excess amount was separated. 50.0 g of toluene was added to the resultant aqueous phase and stirred at room temperature for 30 minutes, and an organic phase containing 2-cyclopropyl-6-methylphenol was separated. This operation was repeated twice. Then, the resultant aqueous solution containing a sodium salt of 6-chloro-3-(2-cyclopropyl-6-methylphenoxy)-4-pyridazinol was quantitatively determined by an HPLC internal standard analysis method, which showed that 6.52 g of 6-chloro-3-(2-cyclopropyl-6-methylphenoxy)-4-pyridazinol (yield: 81%) and 32 mg of 3-chloro-6-(2-cyclopropyl-6-methylphenoxy)-4-pyridazinol (yield: 0.4%) were obtained.

Example 10

Production of 6-chloro-3-(2-cyclopropyl-6-methylphenoxy)-4-pyridazinol

To a mixture of 1.34 g (purity: 96.2%; 34.9 mmol) of 2-cyclopropyl-6-methylphenol and 1,2-dichlorobenzene (42.0 mL) was added 2.06 g (34.9 mmol) of 95% potassium hydroxide at room temperature. The resultant mixture was heated to 180° C. and subjected to azeotropic dehydration under reflux while stirring for one hour. To the resultant solution was added dropwise the preliminarily prepared solution of 3.07 g (purity: 96.0%; 17.8 mmol) of 4-hydroxy-3,6-dichloropyridazine in t-butanol (50.0 g) at 180° C. over 2 hours. (The t-butanol was distilled off simultaneously with the dropwise addition of the solution.) After stirring at 180° C. for another 2 hours, the reaction mixture was cooled to room temperature, and pure water was added to the cooled mixture and stirred at room temperature for 30 minutes, and then an organic phase was separated. 1,2-Dichlorobenzene was added to the resultant aqueous phase and stirred at room temperature for 30 minutes, and then an organic phase containing 2-cyclopropyl-6-methylphenol was separated, and then a 1 N aqueous hydrochloric acid solution and methanol were added to the resultant aqueous phase containing a potassium salt of 6-chloro-3-(2-cyclopropyl-6-methylphenoxy)-4-pyridazinol to obtain a uniform solution. The obtained solution was quantitatively determined by an HPLC internal standard analysis method, which showed that 2.57 g of 6-chloro-3-(2-cyclopropyl-6-methylphenoxy)-4-pyridazinol (yield: 52%) and 29 mg of 3-chloro-6-(2-cyclopropyl-6-methylphenoxy)-4-pyridazinol (yield: 0.6%) were obtained.

Example 11

Production of 6-chloro-3-(2-cyclopropyl-6-methylphenoxy)-4-pyridazinol

To a mixture of 307 mg (purity: 98.0%; 1.82 mmol) of 4-hydroxy-3,6-dichloropyridazine and 833 mg (5.57 mmol) of 2-cyclopropyl-6-methylphenol were added 1-octanol (3.36 mL) and 324 mg (5.50 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 113 mg of 6-chloro-3-(2-cyclopropyl-6-methylphenoxy)-4-pyridazinol (yield: 23%) and 1.4 mg of 3-chloro-6-(2-cyclopropyl-6-methylphenoxy)-4-pyridazinol (yield: 0.3%) were obtained.

Example 12

Production of 6-chloro-3-(2-cyclopropyl-6-methylphenoxy)-4-pyridazinol

To a mixture of 306 mg (purity: 98.0%; 1.82 mmol) of 4-hydroxy-3,6-dichloropyridazine and 821 mg (5.49 mmol) of 2-cyclopropyl-6-methylphenol were added ethyl phenyl ether (2.76 g) and 324 mg (5.50 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 384 mg of 6-chloro-3-(2-cyclopropyl-6-methylphenoxy)-4-pyridazinol (yield: 77%) and 2.0 mg of 3-chloro-6-(2-cyclopropyl-6-methylphenoxy)-4-pyridazinol (yield: 0.4%) were obtained.

Example 13

Production of 6-chloro-3-(2-cyclopropyl-6-methylphenoxy)-4-pyridazinol

To a mixture of 308 mg (purity: 99.0%; 1.85 mmol) of 4-hydroxy-3,6-dichloropyridazine and 2.72 g (18.1 mmol) of 2-cyclopropyl-6-methylphenol was added 331 mg (5.62 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 134 mg of 6-chloro-3-(2-cyclopropyl-6-methylphenoxy)-4-pyridazinol (yield: 26%) was obtained.

Example 14

Production of 6-chloro-3-(2-cyclopropyl-6-methylphenoxy)-4-pyridazinol

To a mixture of 307 mg (purity: 98.0%; 1.82 mmol) of 4-hydroxy-3,6-dichloropyridazine and 828 mg (5.53 mmol) of 2-cyclopropyl-6-methylphenol were added undecane (2.76 g) and 322 mg (5.46 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 340 mg of 6-chloro-3-(2-cyclopropyl-6-methylphenoxy)-4-pyridazinol (yield: 68%) and 1.8 mg of 3-chloro-6-(2-cyclopropyl-6-methylphenoxy)-4-pyridazinol (yield: 0.4%) were obtained.

Example 15

Production of 6-chloro-3-(2-cyclopropyl-6-methylphenoxy)-4-pyridazinol

To a mixture of 308 mg (purity: 99.0%; 1.85 mmol) of 4-hydroxy-3,6-dichloropyridazine and 824 mg (5.47 mmol) of 2-cyclopropyl-6-methylphenol were added sulfolane (2.76 g) and 332 mg (5.63 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 181 mg of 6-chloro-3-(2-cyclopropyl-6-methylphenoxy)-4-pyridazinol (yield: 36%) and 7.1 mg of 3-chloro-6-(2-cyclopropyl-6-methylphenoxy)-4-pyridazinol (yield: 1.4%) were obtained.

Example 16

Production of 6-chloro-3-(2-cyclopropyl-6-methylphenoxy)-4-pyridazinol

To a mixture of 306 mg (purity: 98.0%; 1.82 mmol) of 4-hydroxy-3,6-dichloropyridazine and 825 mg (5.51 mmol) of 2-cyclopropyl-6-methylphenol were added decane (2.76 g) and 327 mg (5.55 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 282 mg of 6-chloro-3-(2-cyclopropyl-6-methylphenoxy)-4-pyridazinol (yield: 56%) and 4.3 mg of 3-chloro-6-(2-cyclopropyl-6-methylphenoxy)-4-pyridazinol (yield: 0.9%) were obtained.

Example 17

Production of 6-chloro-3-(2-cyclopropyl-6-methylphenoxy)-4-pyridazinol

To a mixture of 308 mg (purity: 98.0%; 1.83 mmol) of 4-hydroxy-3,6-dichloropyridazine and 823 mg (5.50 mmol) of 2-cyclopropyl-6-methylphenol were added diphenyl ether (2.76 g) and 328 mg (5.56 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 295 mg of 6-chloro-3-(2-cyclopropyl-6-methylphenoxy)-4-pyridazinol (yield: 58%) and 3.1 mg of 3-chloro-6-(2-cyclopropyl-6-methylphenoxy)-4-pyridazinol (yield: 0.6%) were obtained.

Example 18

Production of 6-chloro-3-(2-cyclopropyl-6-methylphenoxy)-4-pyridazinol

To a mixture of 305 mg (purity: 99.0%; 1.83 mmol) of 4-hydroxy-3,6-dichloropyridazine and 846 mg (5.62 mmol) of 2-cyclopropyl-6-methylphenol were added benzophenone (2.76 g) and 327 mg (5.55 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 314 mg of 6-chloro-3-(2-cyclopropyl-6-methylphenoxy)-4-pyridazinol (yield: 62%) and 3.2 mg of 3-chloro-6-(2-cyclopropyl-6-methylphenoxy)-4-pyridazinol (yield: 0.6%) were obtained.

Example 19

Production of 6-chloro-3-(2-cyclopropyl-6-methylphenoxy)-4-pyridazinol

To a mixture of 306 mg (purity: 98.0%; 1.82 mmol) of 4-hydroxy-3,6-dichloropyridazine and 833 mg (5.53 mmol) of 2-cyclopropyl-6-methylphenol were added quinoline (2.76 g) and 327 mg (5.55 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 321 mg of 6-chloro-3-(2-cyclopropyl-6-methylphenoxy)-4-pyridazinol (yield: 64%) and 3.4 mg of 3-chloro-6-(2-cyclopropyl-6-methylphenoxy)-4-pyridazinol (yield: 0.7%) were obtained.

Example 20

Production of 6-chloro-3-(2-cyclopropyl-6-methylphenoxy)-4-pyridazinol

To a mixture of 306 mg (purity: 99.0%; 1.84 mmol) of 4-hydroxy-3,6-dichloropyridazine and 830 mg (5.51 mmol) of 2-cyclopropyl-6-methylphenol were added dimethylaniline (2.76 g) and 331 mg (5.62 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 381 mg of 6-chloro-3-(2-cyclopropyl-6-methylphenoxy)-4-pyridazinol (yield: 75%) and 3.4 mg of 3-chloro-6-(2-cyclopropyl-6-methylphenoxy)-4-pyridazinol (yield: 0.7%) were obtained.

Example 21

Production of 6-chloro-3-(2-cyclopropyl-6-methylphenoxy)-4-pyridazinol

To a mixture of 306 mg (purity: 99.0%; 1.84 mmol) of 4-hydroxy-3,6-dichloropyridazine and 826 mg (5.48 mmol) of 2-cyclopropyl-6-methylphenol were added benzonitrile (2.76 g) and 323 mg (5.48 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 271 mg of 6-chloro-3-(2-cyclopropyl-6-methylphenoxy)-4-pyridazinol (yield: 53%) was obtained.

Example 22

Production of 6-chloro-3-(2-cyclopropyl-6-methylphenoxy)-4-pyridazinol

To a mixture of 313 mg (purity: 96.0%; 1.82 mmol) of 4-hydroxy-3,6-dichloropyridazine and 824 mg (5.47 mmol) of 2-cyclopropyl-6-methylphenol were added 1,2-dimethoxybenzene (2.76 g) and 326 mg (5.53 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 189 mg of 6-chloro-3-(2-cyclopropyl-6-methylphenoxy)-4-pyridazinol (yield: 38%) was obtained.

Example 23

Production of 6-chloro-3-(2-cyclopropyl-6-methylphenoxy)-4-pyridazinol

To a mixture of 313 mg (purity: 96.0%; 1.82 mmol) of 4-hydroxy-3,6-dichloropyridazine and 839 mg (5.57 mmol) of 2-cyclopropyl-6-methylphenol were added 3-methoxytoluene (2.76 g) and 328 mg (5.56 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 376 mg of 6-chloro-3-(2-cyclopropyl-6-methylphenoxy)-4-pyridazinol (yield: 75%) and 1.9 mg of 3-chloro-6-(2-cyclopropyl-6-methylphenoxy)-4-pyridazinol (yield: 0.4%) were obtained.

Example 24

Production of 6-chloro-3-(2-cyclopropyl-6-methylphenoxy)-4-pyridazinol

To a mixture of 314 mg (purity: 96.0%; 1.83 mmol) of 4-hydroxy-3,6-dichloropyridazine and 828 mg (5.50 mmol) of 2-cyclopropyl-6-methylphenol were added tributylamine (2.76 g) and 334 mg (5.56 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 288 mg of 6-chloro-3-(2-cyclopropyl-6-methylphenoxy)-4-pyridazinol (yield: 57%) and 2.5 mg of 3-chloro-6-(2-cyclopropyl-6-methylphenoxy)-4-pyridazinol (yield: 0.5%) were obtained.

Example 25

Production of 6-chloro-3-(2-cyclopropyl-6-methylphenoxy)-4-pyridazinol

To a mixture of 301 mg (purity: 100%; 1.82 mmol) of 4-hydroxy-3,6-dichloropyridazine and 827 mg (5.49 mmol) of 2-cyclopropyl-6-methylphenol were added decalin (2.76 g) and 326 mg (5.53 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 348 mg of 6-chloro-3-(2-cyclopropyl-6-methylphenoxy)-4-pyridazinol (yield: 69%) and 1.8 mg of 3-chloro-6-(2-cyclopropyl-6-methylphenoxy)-4-pyridazinol (yield: 0.4%) were obtained.

Example 26

Production of 6-chloro-3-(2-cyclopropyl-6-methylphenoxy)-4-pyridazinol

To a mixture of 301 mg (purity: 100%; 1.82 mmol) of 4-hydroxy-3,6-dichloropyridazine and 827 mg (5.49 mmol) of 2-cyclopropyl-6-methylphenol were added N-methylpyrrolidone (2.76 g) and 322 mg (5.46 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 105 mg of 6-chloro-3-(2-cyclopropyl-6-methylphenoxy)-4-pyridazinol (yield: 21%) and 4.2 mg of 3-chloro-6-(2-cyclopropyl-6-methylphenoxy)-4-pyridazinol (yield: 0.8%) were obtained.

Example 27

Production of 6-chloro-3-(2-cyclopropyl-6-methylphenoxy)-4-pyridazinol

To a mixture of 301 mg (purity: 100%; 1.82 mmol) of 4-hydroxy-3,6-dichloropyridazine and 827 mg (5.49 mmol) of 2-cyclopropyl-6-methylphenol were added dipropylaniline (2.76 g) and 325 mg (5.51 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 230 mg of 6-chloro-3-(2-cyclopropyl-6-methylphenoxy)-4-pyridazinol (yield: 46%) and 2.7 mg of 3-chloro-6-(2-cyclopropyl-6-methylphenoxy)-4-pyridazinol (yield: 0.5%) were obtained.

Example 28

Production of 6-chloro-3-(2-cyclopropyl-6-methylphenoxy)-4-pyridazinol

To a mixture of 301 mg (purity: 100%; 1.82 mmol) of 4-hydroxy-3,6-dichloropyridazine and 832 mg (5.52 mmol) of 2-cyclopropyl-6-methylphenol were added normal butylbenzene (2.76 g) and 333 mg (5.65 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 308 mg of 6-chloro-3-(2-cyclopropyl-6-methylphenoxy)-4-pyridazinol (yield: 61%) and 2.9 mg of 3-chloro-6-(2-cyclopropyl-6-methylphenoxy)-4-pyridazinol (yield: 0.6%) were obtained.

Example 29

Production of 6-chloro-3-(2-cyclopropyl-6-methylphenoxy)-4-pyridazinol

To a mixture of 301 mg (purity: 100%; 1.82 mmol) of 4-hydroxy-3,6-dichloropyridazine and 842 mg (5.59 mmol) of 2-cyclopropyl-6-methylphenol were added orthotolunitrile (2.76 g) and 325 mg (5.51 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 277 mg of 6-chloro-3-(2-cyclopropyl-6-methylphenoxy)-4-pyridazinol (yield: 55%) and 3.2 mg of 3-chloro-6-(2-cyclopropyl-6-methylphenoxy)-4-pyridazinol (yield: 0.6%) were obtained.

Example 30

Production of 6-chloro-3-(2-cyclopropyl-6-methylphenoxy)-4-pyridazinol

To a mixture of 302 mg (purity: 100%; 1.83 mmol) of 4-hydroxy-3,6-dichloropyridazine and 826 mg (5.48 mmol) of 2-cyclopropyl-6-methylphenol were added 2-methyl-4-phenylbutanol (2.76 g) and 330 mg (5.60 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 332 mg of 6-chloro-3-(2-cyclopropyl-6-methylphenoxy)-4-pyridazinol (yield: 66%) and 3.6 mg of 3-chloro-6-(2-cyclopropyl-6-methylphenoxy)-4-pyridazinol (yield: 0.7%) were obtained.

Example 31

Production of 6-chloro-3-(2-cyclopropyl-6-methylphenoxy)-4-pyridazinol

To a mixture of 308 mg (purity: 98%; 1.83 mmol) of 4-hydroxy-3,6-dichloropyridazine and 824 mg (5.51 mmol) of 2-cyclopropyl-6-methylphenol were added tetralin (2.76 g) and 334 mg (5.67 mmol) of 95% potassium hydroxide at room temperature. The resultant mixture was heated to 180° C. while stirring, and stirred at that temperature for 4 hours. Then, the resultant reaction mixture was cooled to room temperature, and a 1 N aqueous hydrochloric acid solution and methanol were added to the reaction mixture to obtain a uniform solution. The obtained solution was quantitatively determined by an HPLC internal standard analysis method, which showed that 324 mg of 6-chloro-3-(2-cyclopropyl-6-methylphenoxy)-4-pyridazinol (yield: 64%) and 2.2 mg of 3-chloro-6-(2-cyclopropyl-6-methylphenoxy)-4-pyridazinol (yield: 0.4%) were obtained.

Example 32

Production of 6-chloro-3-(4-t-butylphenoxy)-4-pyridazinol 3.0 g (purity: 90%; 16.4 mmol) of 4-hydroxy-3,6-dichloropyridazine, 7.45 g (49.1 mmol) of 4-t-butylphenol, and 2.03 g (purity: 97%; 49.1 mmol) of sodium hydroxide were added to a mixture of 19.1 g of 1,2-dichlorobenzene and 3.0 g of dimethyl sulfoxide and matured at 180° C. for 8 hours. After completion of the reaction, the reaction mixture was cooled to room temperature, and 50 g of pure water was added to the cooled mixture. A 35% aqueous hydrochloric acid solution was added to the resultant mixture so that the pH of the aqueous phase was adjusted to 2.1, and then the deposited solids were taken out by filtration. The solids were dried under nitrogen gas for 24 hours, and then 25 mL of methyl t-butyl ether was added to the solids to obtain a slurry. After stirring for 1.5 hour, the obtained slurry was subjected to filtration, and the resultant solids were dried under a reduced pressure to obtain 2.61 g of 6-chloro-3-(4-t-butylphenoxy)-4-pyridazinol in the form of pale brown solids (yield: 57.2%).

$^1$H-NMR (400 MHz, DMSO-$d_6$) δ ppm: 7.41 (2H, d, J=8.4 Hz), 7.07 (2H, d, J=8.8 Hz), 6.81 (1H, s), 1.27 (9H, s).

Example 33

Production of 6-chloro-3-[3-(trifluoromethyl)phenoxy]-4-pyridazinol 3.0 g (purity: 90%; 16.4 mmol) of 4-hydroxy-3,6-dichloropyridazine, 7.96 g (49.1 mmol) of 3-trifluoromethylphenol, and 2.03 g (purity: 97%; 49.1 mmol) of sodium hydroxide were added to a mixture of 19.1 g of 1,2-dichlorobenzene and 3.0 g of dimethyl sulfoxide and matured at 180° C. for 8 hours. After completion of the reaction, the reaction mixture was cooled to room temperature, and 50 g of pure water was added to the cooled mixture. A 35% aqueous hydrochloric acid solution was added to the resultant mixture so that the pH of the aqueous phase was adjusted to 2.1, and then the deposited solids were taken out by filtration. 25 mL of methyl t-butyl ether was added to the solids to obtain a slurry. The resultant solids were dried under a reduced pressure to obtain 3.32 g of 6-chloro-3-[3-(trifluoromethyl)phenoxy]-4-pyridazinol in the form of pale brown solids (yield: 69.7%).

$^1$H-NMR (400 MHz, DMSO-$d_6$) δ ppm: 7.70-7.55 (3H, m), 7.51 (1H, d, J=7.6 Hz), 6.85 (1H, s).

Example 34

Production of 6-chloro-3-phenoxy-4-pyridazinol

A mixture of 25.0 g (266 mmol) of phenol and 30.0 g of cyclohexanol was charged, and 25.5 g (266 mmol) of sodium t-butoxide was added to the mixture over one hour, and then stirred at 70° C. for 30 minutes. The resultant solution was cooled to 40° C., and then 8.94 g (purity: 98%; 153.1 mmol) of 4-hydroxy-3,6-dichloropyridazine was added to the cooled solution. Then, the resultant mixture was heated from 40° C. to 140° C. to effect a reaction for 12 hours. After completion of the reaction, the reaction mixture was cooled to room temperature, and 100 g of pure water and 100 g of toluene were added to the cooled mixture, and stirred for 30 minutes. Then, 41.7 g (400 mmol) of a 35% aqueous hydrochloric acid solution was added dropwise to the resultant mixture, and an organic phase containing phenol added in an excess amount was separated. 287 g of toluene was added to the resultant aqueous phase, and stirred at room temperature for 30 minutes, and then an organic phase was separated. Then, the resultant aqueous phase containing a sodium salt of 6-chloro-3-phenoxy-4-pyridazinol was added dropwise to a 35% aqueous hydrochloric acid solution at 0° C. to deposit solids, followed by filtration. The resultant solids were washed with pure water and dried under a reduced pressure, and dissolved in an organic solvent and quantitatively determined by an HPLC area percentage method, which showed that 9.94 g of 6-chloro-3-phenoxy-4-pyridazinol (yield: 84.0%) was obtained.

$^1$H-NMR (400 MHz, DMSO-$d_6$) δ ppm: 7.50-7.35 (2H, m), 7.25-7.13 (3H, m), 6.81 (1H, brs).

Example 35

Production of 6-chloro-3-(2-cyclopropyl-6-methylphenoxy)-4-pyridazinol

To a mixture of 25.5 g (150 mmol) of sodium 2-cyclopropyl-6-methylphenoxide and 12.5 g of t-butanol in an autoclave was added 2.5 g (purity: 99%; 15.0 mmol) of 4-hydroxy-3,6-dichloropyridazine at room temperature. Then, the resultant mixture was heated from room temperature to 140° C. to effect a reaction for 3 hours. After completion of the reaction, the reaction mixture was cooled to room temperature, and 80.0 g of pure water and 90.0 g of toluene were added to the cooled mixture and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 3.74 g of 6-chloro-3-(2-cyclopropyl-6-methylphenoxy)-4-pyridazinol (yield: 90.1%) and 12.5 mg of 3-chloro-6-(2-cyclopropyl-6-methylphenoxy)-4-pyridazinol (yield: 0.3%) were obtained.

Example 36

Production of 6-chloro-3-(2-cyclopropyl-6-methylphenoxy)-4-pyridazinol

A mixture of 114.76 g (purity: 95.9%; 743 mmol) of 2-cyclopropyl-6-methylphenol and 70.0 g of t-butanol was charged into an autoclave, and 72.8 g (purity: 98.0%; 743 mmol) of sodium t-butoxide was added to the mixture over one hour, and then stirred at 70° C. for 30 minutes. The resultant solution was cooled to 40° C., and then 25.0 g (purity: 98%; 148.6 mmol) of 4-hydroxy-3,6-dichloropyridazine was added to the solution. Then, the resultant mixture was heated from 40° C. to 140° C. to effect a reaction for 24 hours. After completion of the reaction, the reaction mixture was cooled to room temperature, and 750 g of pure water and 574 g of toluene were added to the cooled mixture and stirred for 30 minutes. Then, 41.7 g (400 mmol) of a 35% aqueous hydrochloric acid solution was added dropwise to the mixture, and an organic phase containing 2-cyclopropyl-6-methylphenol added in an excess amount was separated. 287 g of toluene was added to the resultant aqueous phase and stirred at room temperature for 30 minutes, and then an organic phase was separated. Then, the resultant aqueous phase containing a sodium salt of 6-chloro-3-(2-cyclopropyl-6-methylphenoxy)-4-pyridazinol was added dropwise to 20.5 g (196 mmol) of a 35% aqueous hydrochloric acid solution at 0° C. to deposit solids, followed by filtration. The resultant solids were washed with pure water and dried under a reduced pressure, and dissolved in an organic solvent and quantitatively determined by an HPLC internal standard analysis method, which showed that 41.2 g of 6-chloro-3-(2-cyclopropyl-6-methylphenoxy)-4-pyridazinol (purity: 85.4%; yield: 87.0%) and 29 mg of 3-chloro-6-(2-cyclopropyl-6-methylphenoxy)-4-pyridazinol (yield: 1.4%) were obtained.

Example 37

Production of 6-chloro-3-(2-cyclopropyl-6-methylphenoxy)-4-pyridazinol

To a mixture of 25.0 g (147 mmol) of sodium 2-cyclopropyl-6-methylphenoxide and 12.5 g of 1-octanol was added 2.5 g (purity: 98.5%; 14.7 mmol) of 4-hydroxy-3,6-dichloropyridazine at room temperature. Then, the resultant mixture was heated from room temperature to 140° C. to effect a reaction for 2 hours. After completion of the reaction, the reaction mixture was cooled to room temperature, and 80.0 g of pure water and 90.0 g of toluene were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 2.81 g of 6-chloro-3-(2-cyclopropyl-6-methylphenoxy)-4-pyridazinol (yield: 69.2%) and 8.0 mg of 3-chloro-6-(2-cyclopropyl-6-methylphenoxy)-4-pyridazinol (yield: 0.2%) were obtained.

Example 38

Production of 6-chloro-3-(2-cyclopropyl-6-methylphenoxy)-4-pyridazinol

To a mixture of 25.5 g (150 mmol) of sodium 2-cyclopropyl-6-methylphenoxide and 12.5 g of 2-octanol was added 2.5 g (purity: 99%; 15.0 mmol) of 4-hydroxy-3,6-dichloropyridazine at room temperature. Then, the resultant mixture was heated from room temperature to 140° C. to effect a reaction for 4 hours. After completion of the reaction, the reaction mixture was cooled to room temperature, and 100 g of pure water and 100 g of toluene were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 3.11 g of 6-chloro-3-(2-cyclopropyl-6-methylphenoxy)-4-pyridazinol (yield: 75.2%) and 10.0 mg of 3-chloro-6-(2-cyclopropyl-6-methylphenoxy)-4-pyridazinol (yield: 0.2%) were obtained.

Example 39

Production of 6-chloro-3-(2-cyclopropyl-6-methylphenoxy)-4-pyridazinol

To a mixture of 25.0 g (147 mmol) of sodium 2-cyclopropyl-6-methylphenoxide and 12.5 g of cyclohexanol was added 2.5 g (purity: 98.5%; 14.7 mmol) of 4-hydroxy-3,6-dichloropyridazine at room temperature. Then, the resultant mixture was heated from room temperature to 140° C. to effect a reaction for 2 hours. After completion of the reaction, the reaction mixture was cooled to room temperature, and 80.0 g of pure water and 90.0 g of toluene were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 3.64 g of 6-chloro-3-(2-cyclopropyl-6-methylphenoxy)-4-pyridazinol (yield: 89.9%) and 10.0 mg of 3-chloro-6-(2-cyclopropyl-6-methylphenoxy)-4-pyridazinol (yield: 0.3%) were obtained.

Example 40

Production of 6-chloro-3-(2-cyclopropyl-6-methylphenoxy)-4-pyridazinol

To a mixture of 25.5 g (150 mmol) of sodium 2-cyclopropyl-6-methylphenoxide and 12.5 g of 2-methylcyclohexanol was added 2.5 g (purity: 99%; 15.0 mmol) of 4-hydroxy-3,6-dichloropyridazine at room temperature. Then, the resultant mixture was heated from room temperature to 140° C. to effect a reaction for 3 hours. After completion of the reaction, the reaction mixture was cooled to room temperature, and 100 g of pure water and 120 g of toluene were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 3.15 g of 6-chloro-3-(2-cyclopropyl-6-methylphenoxy)-4-pyridazinol (yield: 76.0%) and 9.0 mg of 3-chloro-6-(2-cyclopropyl-6-methylphenoxy)-4-pyridazinol (yield: 0.2%) were obtained.

Example 41

Production of 6-chloro-3-(2-cyclopropyl-6-methylphenoxy)-4-pyridazinol

To a mixture of 25.5 g (150 mmol) of sodium 2-cyclopropyl-6-methylphenoxide and 12.5 g of 2-ethyl-1-hexanol was added 2.5 g (purity: 99%; 15.0 mmol) of 4-hydroxy-3,6-dichloropyridazine at room temperature. Then, the resultant mixture was heated from room temperature to 140° C. to effect a reaction for 3 hours. After completion of the reaction, the reaction mixture was cooled to room temperature, and 100 g of pure water and 120 g of toluene were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 2.85 g of 6-chloro-3-(2-cyclopropyl-6-methylphenoxy)-4-pyridazinol (yield: 69.0%) and 9.0 mg of 3-chloro-6-(2-cyclopropyl-6-methylphenoxy)-4-pyridazinol (yield: 0.2%) were obtained.

Example 42

Production of 6-chloro-3-(2-cyclopropyl-6-methylphenoxy)-4-pyridazinol

To a mixture of 25.5 g (150 mmol) of sodium 2-cyclopropyl-6-methylphenoxide and 12.5 g of hexylene glycol was added 2.5 g (purity: 99%; 15.0 mmol) of 4-hydroxy-3,6-dichloropyridazine at room temperature.

Then, the resultant mixture was heated from room temperature to 140° C. to effect a reaction for 3 hours. After completion of the reaction, the reaction mixture was cooled to room temperature, and 100 g of pure water and 100 g of toluene were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 2.21 g of 6-chloro-3-(2-cyclopropyl-6-methylphenoxy)-4-pyridazinol (yield: 53.2%) and 5.0 mg of 3-chloro-6-(2-cyclopropyl-6-methylphenoxy)-4-pyridazinol (yield: 0.1%) were obtained.

Example 43

Production of 6-chloro-3-(2-cyclopropyl-6-methylphenoxy)-4-pyridazinol

To a mixture of 29.8 g (purity: 93.6%; 163 mmol) of sodium 2-cyclopropyl-6-methylphenoxide and 5 g of dimethyl sulfoxide was added 10.0 g (purity: 90%; 54.6 mmol) of 4-hydroxy-3,6-dichloropyridazine at room temperature. Then, the resultant mixture was heated from room temperature to 140° C. to effect a reaction for 28 hours. After completion of the reaction, the reaction mixture was cooled to room temperature, and 300 g of pure water and 200 g of cyclohexane were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 13.3 g of 6-chloro-3-(2-cyclopropyl-6-methylphenoxy)-4-pyridazinol (yield: 87.9%) and 60.4 mg of 3-chloro-6-(2-cyclopropyl-6-methylphenoxy)-4-pyridazinol (yield: 0.4%) were obtained.

Example 44

Production of 6-chloro-3-(2-cyclopropyl-6-methylphenoxy)-4-pyridazinol

To a mixture of 27.4 g (purity: 92.9%; 149 mmol) of sodium 2-cyclopropyl-6-methylphenoxide and 12.5 g of 1,3-dimethyl-2-imidazolidinone was added 2.5 g (purity: 98.5%; 14.9 mmol) of 4-hydroxy-3,6-dichloropyridazine at room temperature. Then, the resultant mixture was heated from room temperature to 140° C. to effect a reaction for 7 hours. After completion of the reaction, the reaction mixture was cooled to room temperature, and 120 g of pure water and 100 g of toluene were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 3.58 g of 6-chloro-3-(2-cyclopropyl-6-methylphenoxy)-4-pyridazinol (yield: 86.9%) and 17 mg of 3-chloro-6-(2-cyclopropyl-6-methylphenoxy)-4-pyridazinol (yield: 0.4%) were obtained.

Example 45

Production of 6-chloro-3-(2-cyclopropyl-6-methylphenoxy)-4-pyridazinol

To a mixture of 27.4 g (purity: 92.9%; 149 mmol) of sodium 2-cyclopropyl-6-methylphenoxide and 12.5 g of cyclohexanone was added 2.5 g (purity: 98.5%; 14.9 mmol) of 4-hydroxy-3,6-dichloropyridazine at room temperature. Then, the resultant mixture was heated from room temperature to 140° C. to effect a reaction for 7 hours. After completion of the reaction, the reaction mixture was cooled to room temperature, and 120 g of pure water and 100 g of toluene were added to the cooled mixture, and stirred for 30 minutes, and an organic phase containing 2-cyclopropyl-6-methylphenol added in an excess amount was separated. Then, the resultant aqueous phase containing a sodium salt of 6-chloro-3-(2-cyclopropyl-6-methylphenoxy)-4-pyridazinol was quantitatively determined by an HPLC internal standard analysis method, which showed that 2.48 g of 6-chloro-3-(2-cyclopropyl-6-methylphenoxy)-4-pyridazinol (yield: 60.2%) and 16 mg of 3-chloro-6-(2-cyclopropyl-6-methylphenoxy)-4-pyridazinol (yield: 0.4%) were obtained.

Example 46

Production of 6-chloro-3-(2-cyclopropyl-6-methylphenoxy)-4-pyridazinyl morpholine-4-carboxylate To 19.0 g (68.8 mmol) of 6-chloro-3-(2-cyclopropyl-6-methylphenoxy)-4-pyridazinol were added 51.3 g of acetone and 10.5 g (75.7 mmol) of potassium carbonate, and the resultant mixture was stirred at 30° C. To the mixture was added dropwise 11.3 g (75.7 mmol) of morpholinecarbonyl chloride over one hour. The reaction mixture was subjected to reaction at 30° C. for 5 hours. After completion of the reaction, pure water was added to the reaction mixture to deposit solids, and then the solids were taken out by filtration. The resultant solids were dried under a reduced pressure, and the solids were quantitatively determined by an HPLC internal standard analysis method, which showed that 26.6 g of 6-chloro-3-(2-cyclopropyl-6-methylphenoxy)-4-pyridazinyl morpholine-4-carboxylate (yield: 99%) was obtained.

Example 47

Production of 6-chloro-3-(2-cyclopropyl-6-methylphenoxy)-4-pyridazinyl morpholine-4-carboxylate To 6.50 g (23.5 mmol) of 6-chloro-3-(2-cyclopropyl-6-methylphenoxy)-4-pyridazinol were added 39 g of toluene and 2.62 g (25.9 mmol) of triethylamine, and the resultant mixture was stirred at 30° C. To the mixture was added dropwise 7.73 g (51.7 mmol) of morpholinecarbonyl chloride over one hour. The reaction mixture was subjected to reaction at 30° C. for 2 hours, and then further heated to 50° C. to effect a reaction for 2 hours. After completion of the reaction, pure water was added to the reaction mixture, and an organic phase and an aqueous phase were separated, and then the resultant organic phase was quantitatively determined by an HPLC internal standard analysis method, which showed that 9.07 g of 6-chloro-3-(2-cyclopropyl-6-methylphenoxy)-4-pyridazinyl morpholine-4-carboxylate (yield: 99%) was obtained.

Example 48

Production of 6-chloro-3-(2-cyclopropyl-6-methylphenoxy)-4-pyridazinyl morpholine-4-carboxylate To 6.50 g (23.5 mmol) of 6-chloro-3-(2-cyclopropyl-6-methylphenoxy)-4-pyridazinol were added 39 g of butyl acetate and 3.57 g (25.9 mmol) of potassium carbonate, and the resultant mixture was stirred at 50° C. To the mixture was added dropwise 3.87 g (25.9 mmol) of morpholinecarbonyl chloride over one hour. The reaction mixture was subjected to reaction at 50° C. for 6 hours. After completion of the reaction, the resultant opaque mixture was subjected to filtration, and washed with butyl acetate, and then the resultant organic phase was quantitatively determined by an HPLC internal standard analysis method, which showed that 9.09 g of 6-chloro-3-(2-cyclopropyl-6-methylphenoxy)-4-pyridazinyl morpholine-4-carboxylate (yield: 99%) was obtained.

Example 49

Production of 6-chloro-3-(2-cyclopropyl-6-methylphenoxy)-4-pyridazinyl morpholine-4-carboxylate To 6.50 g (23.5 mmol) of 6-chloro-3-(2-cyclopropyl-6-methylphenoxy)-4-pyridazinol were added 39 g of methyl isobutyl ketone and 3.57 g (25.9 mmol) of potassium carbonate, and the resultant mixture was stirred at 50° C. To the mixture was added dropwise 3.87 g (25.9 mmol) of morpholinecarbonyl chloride over one hour. The reaction mixture was subjected to reaction at 50° C. for 4 hours. After completion of the reaction, the resultant opaque mixture was subjected to filtration, and washed with methyl isobutyl ketone, and then the resultant organic phase was quantitatively determined by an HPLC internal standard analysis method, which showed that 9.00 g of 6-chloro-3-(2-cyclopropyl-6-methylphenoxy)-4-pyridazinyl morpholine-4-carboxylate (yield: 98%) was obtained.

Reference Example 1

Preparation of sodium 2-cyclopropyl-6-methylphenoxide 115.4 g of pure water was added to 54.1 g (1.312 mol) of 97% sodium hydroxide and heated to 50° C. to dissolve sodium hydroxide, and then xylene (1,000 ml) was added to the resultant solution at room temperature. To the mixture was added dropwise 200 g (1.317 mol) of 2-cyclopropyl-6-methylphenol at room temperature over 20 minutes. The resultant two-phase solution was subjected to thermal dehydration at 140° C., and, after completion of the distilling off of water, the resultant solution was cooled to 5° C. to obtain a slurry. The obtained slurry was subjected to filtration under a reduced pressure, and the resultant solids were washed with 500 ml of hexane twice. The solids were dried under a reduced pressure, and the resultant solids were quantitatively determined by an HPLC internal standard analysis method, which showed that 150.2 g of sodium 2-cyclopropyl-6-methylphenoxide (yield: 67%) was obtained.

INDUSTRIAL APPLICABILITY

According to the present invention, a 3-(substituted oxy)-4-pyridazinol derivative (I) and a 3-(substituted oxy)-4-pyridazinyl 4-morpholinecarboxylate (V) can be provided in high yield and with high selectivity at a low cost, and therefore various functional and active substances can be advantageously synthesized using the above compound as a medicine, an agricultural chemical, a functional material, or an intermediate thereof.

The invention claimed is:
1. A method for producing a 3-(substituted oxy)-4-pyridazinol compound represented by the following general formula (I):

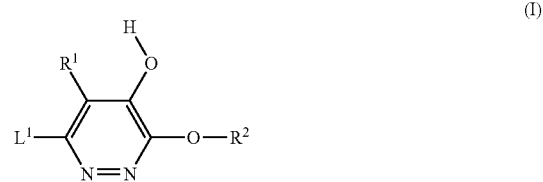

wherein:

$R^1$ represents a hydrogen atom, a halogen atom, a $C_1$-$C_3$ alkyl group, a ($C_1$-$C_3$ alkoxy)$C_1$-$C_3$ alkyl group, or a tri($C_1$-$C_3$ alkyl)silyl group;

$R^2$ represents a $C_1$-$C_6$ alkyl group, a $C_1$-$C_6$ haloalkyl group, a $C_3$-$C_6$ cycloalkyl group, a $C_2$-$C_6$ alkenyl group, a ($C_1$-$C_6$ alkoxy)$C_1$-$C_6$ alkyl group, a 5- or 6-membered heterocyclic group (in which the heterocycle contains in the ring thereof one of a nitrogen atom, an oxygen atom, or a sulfur atom and optionally further contains 1 to 2 nitrogen atoms), or an optionally substituted phenyl group represented by the following general formula (II):

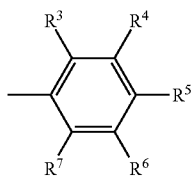

(II)

wherein, in the general formula (II), each of $R^3$, $R^4$, $R^5$, $R^6$, and $R^7$ independently represents a hydrogen atom, a fluorine atom, a chlorine atom, a bromine atom, an iodine atom, an optionally substituted $C_1$-$C_4$ alkyl group (in which the substituent is 1 to 3 substituents which are selected from the group consisting of a fluorine atom, a chlorine atom, and a bromine atom, and which are the same or different, or a $C_3$-$C_4$ cycloalkyl group, a $C_1$-$C_3$ alkylthio group, or a $C_1$-$C_3$ alkoxyimino group), a $C_2$-$C_3$ alkenyl group, a $C_2$-$C_3$ alkynyl group, an optionally substituted $C_3$-$C_5$ cycloalkyl group (in which the substituent is 1 to 3 substituents which are selected from the group consisting of a fluorine atom, a chlorine atom, a bromine atom, a $C_1$-$C_3$ alkyl group, a $C_3$-$C_4$ cycloalkyl group, a cyano group, a $C_1$-$C_3$ alkoxy group, and a $C_1$-$C_3$ alkylthio group, and which are the same or different), a $C_6$-$C_7$ bicycloalkyl group, a cyano group, a $C_2$-$C_4$ alkylcarbonyl group, a $C_2$-$C_4$ alkoxycarbonyl group, an optionally substituted phenyl group {in which the substituent is a fluorine atom, a chlorine atom, a bromine atom, a $C_1$-$C_3$ alkyl group, or a $C_1$-$C_3$ haloalkyl group (in which the halogen atom is 1 to 3 halogen atoms which are selected from the group consisting of a fluorine atom, a chlorine atom, and a bromine atom, and which are the same or different)}, an optionally substituted 5- or 6-membered heterocyclic group {in which the heterocycle contains in the ring thereof one of a nitrogen atom, an oxygen atom, or a sulfur atom and optionally further contains 1 to 2 nitrogen atoms, and the substituent is 1 to 2 substituents which are selected from the group consisting of a fluorine atom, a chlorine atom, a bromine atom, a $C_1$-$C_3$ alkyl group, and a $C_1$-$C_3$ haloalkyl group (in which the halogen atom is 1 to 3 halogen atoms which are selected from the group consisting of a fluorine atom, a chlorine atom, and a bromine atom, and which are the same or different), and which are the same or different}, a nitro group, a $C_1$-$C_3$ alkoxy group, a $C_1$-$C_3$ haloalkoxy group (in which the halogen atom is 1 to 3 halogen atoms which are selected from the group consisting of a fluorine atom, a chlorine atom, and a bromine atom, and which are the same or different), an optionally substituted phenoxy group (in which the substituent is a pyridazinyloxy group substituted with 1 to 3 substituents which are selected from the group consisting of a fluorine atom, a chlorine atom, a bromine atom, and a $C_1$-$C_3$ alkoxy group, and which are the same or different), or a $C_1$-$C_3$ alkylthio group, or a group which the adjacent two of $R^3$, $R^4$, $R^5$, $R^6$, and $R^7$ taken together form is a group represented by the formula:
—$CH_2CH_2$—, —$CH_2CH_2CH_2$—, —$CH(CH_3)CH_2CH_2$—, —$CH_2CH_2CH_2CH_2$—, —$CH$=$CH$—$CH$=$CH$—, —$OCH_2CH_2$—, —$OCH$=$CH$—, —$OCH$=$C(CH_3)$—, —$SCH$=$CH$—, —$N$=$CH$—$CH$=$CH$—, —$OCH_2O$—, —$OCH_2CH_2O$—,

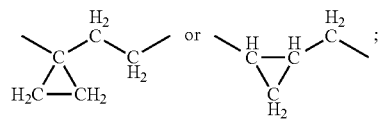

and $L^1$ represents a halogen atom, a cyano group, an $OR^8$ group {wherein $R^8$ is an optionally substituted phenyl group (in which the substituent is 1 to 3 substituents which are selected from the group consisting of a nitro group, a trifluoromethyl group, and a cyano group, and which are the same or different)}, an $SO_2R^9$ group {wherein $R^9$ is a $C_1$-$C_6$ alkyl group, a $C_1$-$C_6$ haloalkyl group, or an optionally substituted phenyl group (in which the substituent is 1 to 3 substituents which are selected from the group consisting of a $C_1$-$C_6$ alkyl group, a halogen atom, a nitro group, a trifluoromethyl group, and a cyano group, and which are the same or different)}, a nitro group, an imidazolyl group, or a pyrazolyl group, the method comprising:

reacting a compound represented by the following general formula (III):

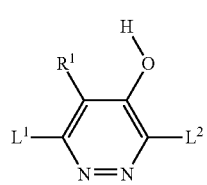

(III)

wherein $R^1$ and $L^1$ are as defined above, and $L^2$ represents a halogen atom, a cyano group, or an $OR^8$ group {wherein $R^8$ is an optionally substituted phenyl group (in which the substituent is 1 to 3 substituents which are selected from the group consisting of a nitro group, a trifluoromethyl group, and a cyano group, and which are the same or different)}, an $SO_2R^9$ group {wherein $R^9$ is a $C_1$-$C_6$ alkyl group, a $C_1$-$C_6$ haloalkyl group, or an optionally substituted phenyl group (in which the substituent is 1 to 3 substituents which are selected from the group consisting of a $C_1$-$C_6$ alkyl group, a halogen atom, a nitro group, a trifluoromethyl group, and a cyano group, and which are the same or different)}, a nitro group, an imidazolyl group, or a pyrazolyl group, and $L^1$ and $L^2$ are the same or different with a compound represented by the following general formula (IV):

  (IV)

wherein M represents a hydrogen atom or an alkali metal, and $R^2$ is as defined above in the presence or absence of a base and in the presence or absence of a solvent to produce a 3-(substituted oxy)-4-pyridazinol compound represented by the general formula (I), wherein the base used is a metal hydroxide, a metal carbonate, a metal hydrogencarbonate, a metal alkoxide, an organic acid metal salt, a metal hydride, a metal, an amine, metal amide or an organometallic base, and wherein when the base is absent or an amine, M is an alkali metal.

2. The method according to claim 1, wherein, in the general formula (I), $R^1$ is a hydrogen atom, $L^1$ is a halogen atom, and $R^2$ is an optionally substituted phenyl group represented by the general formula (II), wherein, in the general formula (II), each of $R^3$, $R^4$, $R^5$, $R^6$, and $R^7$ is independently a hydrogen atom, a fluorine atom, a chlorine atom, a bromine atom, an iodine atom, an optionally substituted $C_1$-$C_4$ alkyl group (in which the substituent is 1 to 3 substituents which are selected from the group consisting of a fluorine atom, a chlorine atom, and a bromine atom, and which are the same or different, or a $C_3$-$C_4$ cycloalkyl group, a $C_1$-$C_3$ alkylthio group, or a $C_1$-$C_3$ alkoxyimino group), a $C_2$-$C_3$ alkenyl group, a $C_2$-$C_3$ alkynyl group, an optionally substituted $C_3$-$C_5$ cycloalkyl group (in which the substituent is 1 to 3 substituents which are selected from the group consisting of a fluorine atom, a chlorine atom, a bromine atom, a $C_1$-$C_3$ alkyl group, a $C_3$-$C_4$ cycloalkyl group, a cyano group, a $C_1$-$C_3$ alkoxy group, and a $C_1$-$C_3$ alkylthio group, and which are the same or different), a $C_6$-$C_7$ bicycloalkyl group, a cyano group, a $C_2$-$C_4$ alkylcarbonyl group, a $C_2$-$C_4$ alkoxycarbonyl group, an optionally substituted phenyl group {in which the substituent is a fluorine atom, a chlorine atom, a bromine atom, a $C_1$-$C_3$ alkyl group, or a $C_1$-$C_3$ haloalkyl group (in which the halogen atom is 1 to 3 halogen atoms which are selected from the group consisting of a fluorine atom, a chlorine atom, and a bromine atom, and which are the same or different)}, an optionally substituted 5- or 6-membered heterocyclic group {in which the heterocycle contains in the ring thereof one of a nitrogen atom, an oxygen atom, or a sulfur atom and optionally further contains 1 to 2 nitrogen atoms, and the substituent is 1 to 2 substituents which are selected from the group consisting of a fluorine atom, a chlorine atom, a bromine atom, a $C_1$-$C_3$ alkyl group, and a $C_1$-$C_3$ haloalkyl group (in which the halogen atom is 1 to 3 halogen atoms which are selected from the group consisting of a fluorine atom, a chlorine atom, and a bromine atom, and which are the same or different), and which are the same or different}, a nitro group, a $C_1$-$C_3$ alkoxy group, a $C_1$-$C_3$ haloalkoxy group (in which the halogen atom is 1 to 3 halogen atoms which are selected from the group consisting of a fluorine atom, a chlorine atom, and a bromine atom, and which are the same or different), an optionally substituted phenoxy group (in which the substituent is a pyridazinyloxy group substituted with 1 to 3 substituents which are selected from the group consisting of a fluorine atom, a chlorine atom, a bromine atom, and a $C_1$-$C_3$ alkoxy group, and which are the same or different), or a $C_1$-$C_3$ alkylthio group, or the group which the adjacent two of $R^3$, $R^4$, $R^5$, $R^6$, and $R^7$ taken together form is a group represented by the formula: —$CH_2CH_2$—, —$CH_2CH_2CH_2$—, —$CH(CH_3)CH_2CH_2$—, —$CH_2CH_2CH_2CH_2$—, —CH=CH—CH=CH—, —$OCH_2CH_2$—, —OCH=CH—, —OCH=CH—, —OCH=C($CH_3$)—, —SCH=CH—, —N=CH—CH=CH—, —$OCH_2O$—, —$OCH_2CH_2O$—,

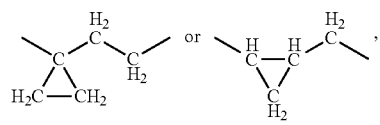

and wherein, in the general formula (III), $L^2$ is a halogen atom.

3. The method according to claim 1, wherein, in the general formula (I), $R^1$ is a hydrogen atom, $L^1$ is a chlorine atom, and $R^2$ is an optionally substituted phenyl group represented by the general formula (II), wherein, in the general formula (II), each of $R^3$, $R^4$, $R^5$, $R^6$, and $R^7$ is independently a hydrogen atom, a fluorine atom, a chlorine atom, a bromine atom, an iodine atom, an optionally substituted $C_1$-$C_4$ alkyl group (in which the substituent is 1 to 3 fluorine atoms, or a $C_3$-$C_4$ cycloalkyl group, or a $C_1$-$C_3$ alkylthio group), a $C_2$-$C_3$ alkenyl group, a $C_2$-$C_3$ alkynyl group, an optionally substituted $C_3$-$C_5$ cycloalkyl group (in which the substituent is 1 to 3 substituents which are selected from the group consisting of a fluorine atom, a chlorine atom, a $C_1$-$C_3$ alkyl group, a $C_3$-$C_4$ cycloalkyl group, a $C_1$-$C_3$ alkoxy group, and a $C_1$-$C_3$ alkylthio group, and which are the same or different), a $C_6$-$C_7$ bicycloalkyl group, an optionally substituted phenyl group {in which the substituent is a fluorine atom, a chlorine atom, a bromine atom, a $C_1$-$C_3$ alkyl group, or a $C_1$-$C_3$ haloalkyl group (in which the halogen atom is 1 to 3 fluorine atoms)}, an optionally substituted 5- or 6-membered heterocyclic group {in which the heterocycle contains in the ring thereof one of a nitrogen atom, an oxygen atom, or a sulfur atom and optionally further contains 1 to 2 nitrogen atoms, and the substituent is 1 to 2 substituents which are selected from the group consisting of a fluorine atom, a chlorine atom, a bromine atom, a $C_1$-$C_3$ alkyl group, and a $C_1$-$C_3$ haloalkyl group (in which the halogen atom is 1 to 3 fluorine atoms), and which are the same or different}, a nitro group, a $C_1$-$C_3$ alkoxy group, a $C_1$-$C_3$ haloalkoxy group (in which the halogen atom is 1 to 3 fluorine atoms), an optionally substituted phenoxy group (in which the substituent is a pyridazinyloxy group substituted with 1 to 2 substituents which are selected from the group consisting of a fluorine atom, a chlorine atom, a bromine atom, and a $C_1$-$C_3$ alkoxy group, and which are the same or different), or a $C_1$-$C_3$ alkylthio group, or the group which the adjacent two of $R^3$, $R^4$, $R^5$, $R^6$, and $R^7$ taken together form is a group represented by the formula: —$CH_2CH_2$—, —$CH_2CH_2CH_2$—, —$CH(CH_3)CH_2CH_2$—, —$CH_2CH_2CH_2CH_2$—, —CH=CH—CH=CH—, —$OCH_2CH_2$—, —OCH=CH—, —OCH=C($CH_3$)—, —SCH=CH—, —N=CH—CH=CH—, —$OCH_2O$—, —$OCH_2CH_2O$—,

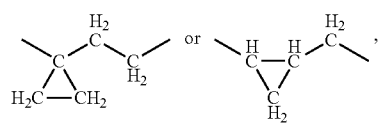

and wherein, in the general formula (III), $L^2$ is a chlorine atom, a bromine atom, or an iodine atom.

4. The method according to claim 1, wherein, in the general formula (I), $R^1$ is a hydrogen atom, $L^1$ is a chlorine atom, and $R^2$ is an optionally substituted phenyl group represented by the general formula (II), wherein, in the general formula (II), each of $R^3$, $R^4$, $R^5$, $R^6$, and $R^7$ is independently a hydrogen atom, a fluorine atom, a chlorine atom, a bromine atom, an iodine atom, a $C_1$-$C_4$ alkyl group, or a $C_3$-$C_5$ cycloalkyl group, or the group which the adjacent two of $R^3$, $R^4$, $R^5$, $R^6$, and $R^7$ taken together form is a group represented by the formula: —$CH_2CH_2CH_2$—, and wherein, in the general formula (III), $L^2$ is a chlorine atom, a bromine atom, or an iodine atom.

5. The method according to claim 1, wherein, in the general formula (I), $R^1$ is a hydrogen atom, $L^1$ is a chlorine atom, and $R^2$ is an optionally substituted phenyl group represented by the general formula (II), wherein, in the general formula (II), each of $R^3$, $R^4$, $R^5$, $R^6$, and $R^7$ is independently a hydrogen atom, a fluorine atom, a chlorine atom, a bromine atom, an iodine atom, a $C_1$-$C_4$ alkyl group, or a $C_3$-$C_5$ cycloalkyl group, and wherein, in the general formula (III), $L^2$ is a chlorine atom, a bromine atom, or an iodine atom.

6. The method according to claim 1, wherein, in the general formula (I), $R^1$ is a hydrogen atom, $L^1$ is a chlorine atom, and $R^2$ is an optionally substituted phenyl group represented by the general formula (II), wherein, in the general formula (II), each of $R^3$, $R^4$, $R^5$, $R^6$, and $R^7$ is independently a hydrogen atom, a methyl group, or a cyclopropyl group, and wherein, in the general formula (III), $L^2$ is a chlorine atom, a bromine atom, or an iodine atom.

7. The method according to claim 1, wherein, in the general formula (I), $R^1$ is a hydrogen atom, $L^1$ is a chlorine atom, and $R^2$ is a 2-cyclopropyl-6-methylphenyl group, and wherein, in the general formula (III), $L^2$ is a chlorine atom.

8. The method according to claim 1, wherein the base used is an alkali metal hydroxide, an alkaline earth metal hydroxide, an alkali metal carbonate, an alkaline earth metal carbonate, an alkali metal hydrogencarbonate, an alkali metal alkoxide, an alkaline earth metal alkoxide, an organic acid alkali metal salt, an organic acid alkaline earth metal salt, an alkali metal hydride, an alkaline earth metal hydride, an alkali metal, an alkaline earth metal, an aliphatic tertiary amine, an alicyclic tertiary amine, an aromatic tertiary amine, a pyridine, a metal amide, or an organometallic base.

9. The method according to claim 1, wherein the base used is lithium hydroxide, sodium hydroxide, potassium hydroxide, cesium hydroxide; lithium methoxide, lithium ethoxide, lithium t-butoxide, lithium t-amyloxide, lithium 2,6-di-t-butylphenoxide, lithium 2,6-di-t-butyl-4-methylphenoxide, sodium methoxide, sodium ethoxide, sodium t-butoxide, sodium t-amyloxide, sodium 2,6-di-t-butylphenoxide, sodium 2,6-di-t-butyl-4-methylphenoxide, potassium methoxide, potassium ethoxide, potassium t-butoxide, potassium t-amyloxide, potassium 2,6-di-t-butylphenoxide, potassium 2,6-di-t-butyl-4-methylphenoxide, rubidium t-butoxide, cesium t-butoxide; lithium hydride, sodium hydride, potassium hydride; lithium, sodium, potassium; lithium amide, sodium amide, potassium amide, lithium diethylamide, lithium diisopropylamide, lithium cyclohexylisopropylamide, lithium tetramethylpiperazide, lithium bis(trimethylsilyl)amide, sodium bis(trimethylsilyl)amide, potassium bis(trimethylsilyl)amide; or methyllithium, n-butyllithium, s-butyllithium, t-butyllithium, phenyllithium, sodium naphthalene, potassium naphthalene, potassium diphenylethylene, benzylpotassium, cumylpotassium, or cumylcesium.

10. The method according to claim 1, wherein the base used is sodium hydroxide, potassium hydroxide; sodium methoxide, sodium ethoxide, sodium t-butoxide, potassium t-butoxide; sodium hydride, potassium hydride; sodium, potassium; or sodium amide, potassium amide, sodium bis(trimethylsilyl)amide, or potassium bis(trimethylsilyl)amide.

11. The method according to claim 1, wherein the base used is sodium hydroxide, potassium hydroxide; sodium t-butoxide, potassium t-butoxide; sodium hydride, potassium hydride; or sodium amide, or potassium amide.

12. The method according to claim 1, wherein the base used is sodium hydroxide, potassium hydroxide; or sodium t-butoxide, or potassium t-butoxide.

13. The method according to claim 1, wherein M in the general formula (IV) is a hydrogen atom.

14. The method according to claim 1, wherein M in the general formula (IV) is an alkali metal.

15. The method according to claim 14, wherein M in the general formula (IV) is sodium.

16. The method according to claim 14, wherein the reaction between the compound represented by the general formula (III) and the compound represented by the general formula (IV) is conducted in the absence of a base.

17. A method for producing a 3-(substituted oxy)-4-pyridazinyl 4-morpholinecarboxylate represented by the following general formula (V):

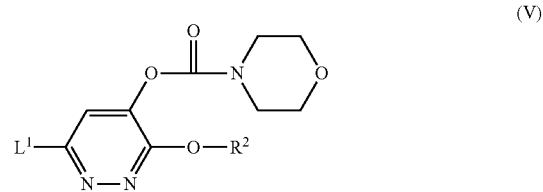

the method comprising producing:

in accordance with the method according to claim 1, obtaining a compound represented by the following general formula (I) in accordance with the method of claim 1:

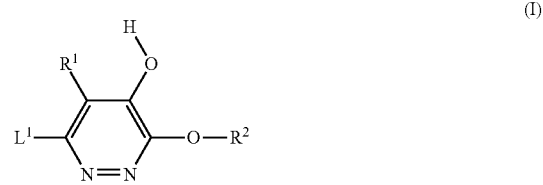

wherein $R^1$, $R^2$, and $L^1$ are as defined in claim 1, and reacting the obtained compound represented by the general formula (I) with a compound represented by the following general formula (VI):

wherein X is a chlorine atom, a bromine atom, or an iodine atom in the presence of a base and in the presence or absence of a solvent to produce a 3-(substituted oxy)-4-pyridazinyl 4-morpholinecarboxylate represented by the general formula (V).

* * * * *